(12) United States Patent
Hanada et al.

(10) Patent No.: US 10,729,629 B2
(45) Date of Patent: Aug. 4, 2020

(54) COMPLEX AND EMULSION COMPOSITION

(71) Applicant: Kokyu Alcohol Kogyo Co., Ltd., Narita-shi, Chiba (JP)

(72) Inventors: Naomi Hanada, Narita (JP); Takayuki Omura, Narita (JP)

(73) Assignee: Kokyu Alcohol Kogyo Co., Ltd., Narita-shi, Chiba (JP)

( * ) Notice: Subject to any disclaimer, the term of this patent is extended or adjusted under 35 U.S.C. 154(b) by 17 days.

(21) Appl. No.: 16/155,954

(22) Filed: Oct. 10, 2018

(65) Prior Publication Data

US 2019/0125644 A1 May 2, 2019

(30) Foreign Application Priority Data

Nov. 1, 2017 (JP) ................................. 2017-211829
Nov. 21, 2017 (JP) ................................. 2017-224019
Apr. 27, 2018 (JP) ................................. 2018-086796

(51) Int. Cl.

| | | |
|---|---|---|
| A61K 8/42 | (2006.01) | |
| A61Q 19/00 | (2006.01) | |
| A61K 8/81 | (2006.01) | |
| B01F 17/00 | (2006.01) | |
| A61K 8/06 | (2006.01) | |
| A61Q 19/02 | (2006.01) | |
| A61Q 17/04 | (2006.01) | |
| A61Q 5/12 | (2006.01) | |
| A61Q 1/02 | (2006.01) | |

(52) U.S. Cl.
CPC .............. *A61K 8/42* (2013.01); *A61K 8/062* (2013.01); *A61K 8/064* (2013.01); *A61K 8/8141* (2013.01); *A61K 8/8147* (2013.01); *A61Q 1/02* (2013.01); *A61Q 5/12* (2013.01); *A61Q 17/04* (2013.01); *A61Q 19/00* (2013.01); *A61Q 19/02* (2013.01); *B01F 17/0042* (2013.01); *B01F 17/0085* (2013.01)

(58) Field of Classification Search
None
See application file for complete search history.

(56) References Cited

U.S. PATENT DOCUMENTS

| | | |
|---|---|---|
| 2,922,740 A | 1/1960 | Williams et al. |
| 3,647,738 A | 3/1972 | Foster et al. |
| 4,325,973 A | 4/1982 | Graham et al. |
| 4,749,563 A | 6/1988 | Georgalas |
| 5,866,040 A | 2/1999 | Nakama et al. |
| 2004/0228811 A1 | 11/2004 | Krzysik |

FOREIGN PATENT DOCUMENTS

| | | |
|---|---|---|
| DE | 1920975 A1 | 11/1969 |
| EP | 0500941 A1 | 9/1992 |
| GB | 1447454 A | 8/1976 |
| JP | 50-17216 A | 2/1975 |
| JP | 61-114724 A | 6/1986 |
| JP | H01-502116 A | 7/1989 |
| JP | H06-65596 A | 3/1994 |
| JP | H07-126233 A | 5/1995 |
| JP | 08-029934 A | 2/1996 |
| JP | 2003-176210 A | 6/2003 |
| JP | 2005-060457 A | 3/2005 |
| WO | WO 88/04167 A1 | 6/1988 |

OTHER PUBLICATIONS

PubChem SID Schem BL8828937 (deposited and available on Feb. 2, 2015).*

* cited by examiner

*Primary Examiner* — Jeffrey T. Palenik
(74) *Attorney, Agent, or Firm* — Wolf, Greenfield & Sacks, P.C.

(57) ABSTRACT

[Problem] An object of the invention is to provide a novel complex that can be used as an emulsifier.
[Solving means] A complex in which an amide alcohol and a carboxyl group-containing polymer exerts an excellent emulsifying power for oil having a wide range of required HLB.

10 Claims, 13 Drawing Sheets

Comparative formulation 8 (ARISTOFLEX HMB)

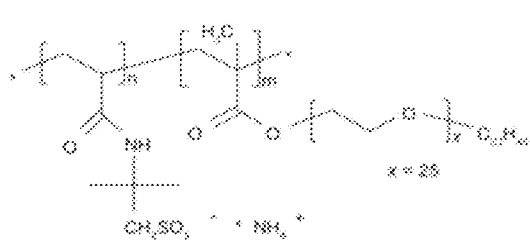

ARISTOFLEX HMB
Having emulsifying ability
due to EO possessed in a molecule

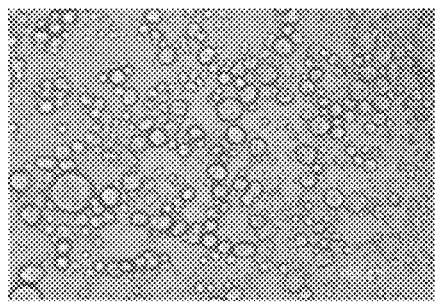

Non-neutralized
Emulsion particle size : ~30(50) μm
Viscosity : 1590 mPa·s
pH : 7.56

Fig. 7

Comparison of comparative formulation 7 (ARISTOFELX HMB alone)
and comparative formulation 6 (combined use of ARISTOFELX HMB/amide alcohol of structural formula (II))

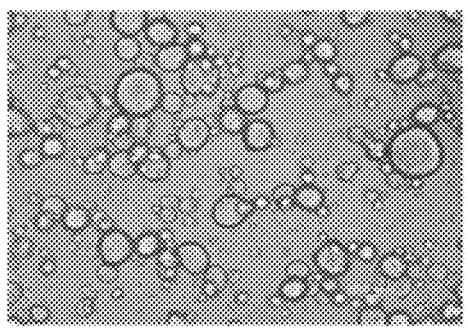

Comparative formulation 7
ARISTOFELX HMB alone
Emulsion particle size : ~30(50) μm
pH : 7.79

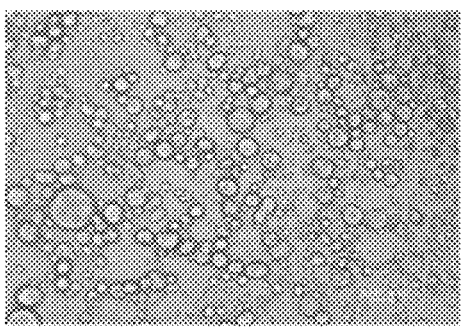

Comparative formulation 6
Combined use of ARISTOFELX HMB/amide alcohol of structural formula (I)
Emulsion particle size : ~30(50) μm
pH : 6.76

Fig. 8

Basic formulation 2 (squalene, neutralizing agent: triethanolamine)
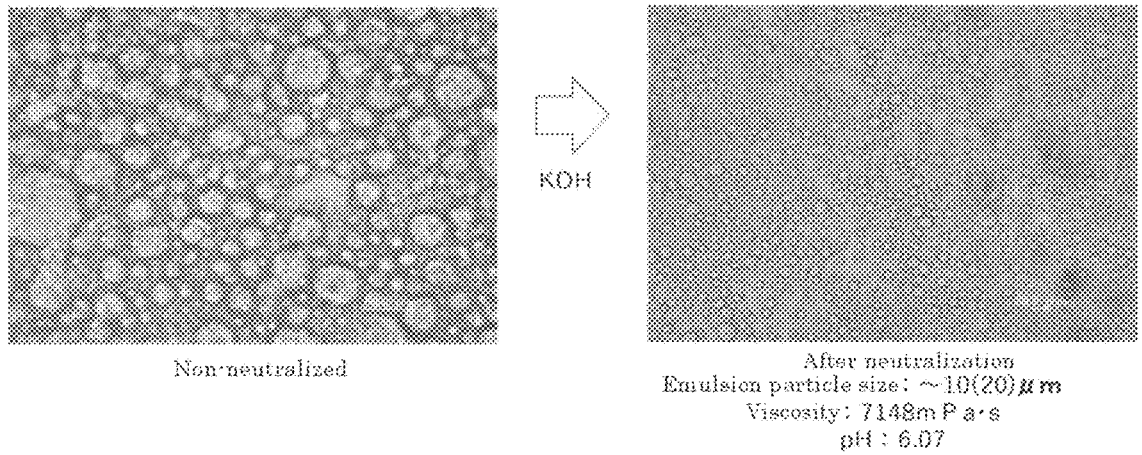
Fig. 9
Comparative formulation 8 (amide alcohol of structural formula (II) not blended, Acrylate/C10-30 Alkyl Acrylates Crosspolymer blended)
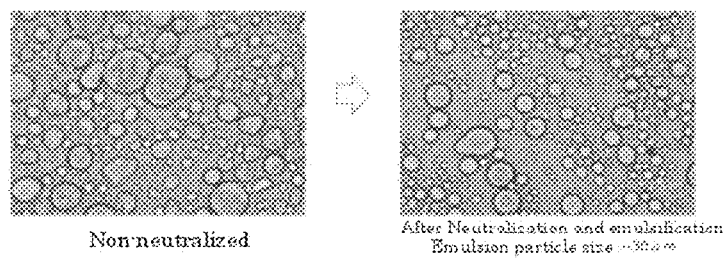
Example 3 (amide alcohol of structural formula (II) blended, Acrylate/C10-30 Alkyl Acrylates Crosspolymer blended)
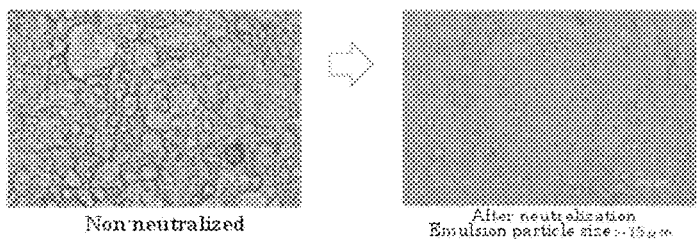
Fig. 10

Example A (LH)
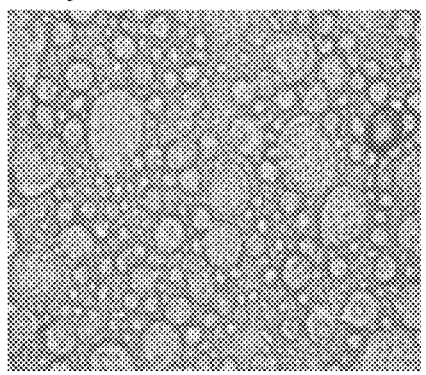  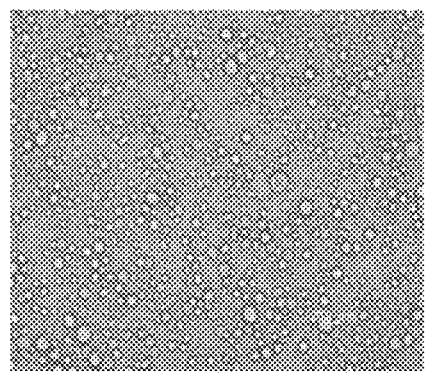
Non-neutralized
After neutralization
Emulsion particle size : ~5(20)μm
Viscosity : 48960mPa·s
pH : 6.77
Example (LB)
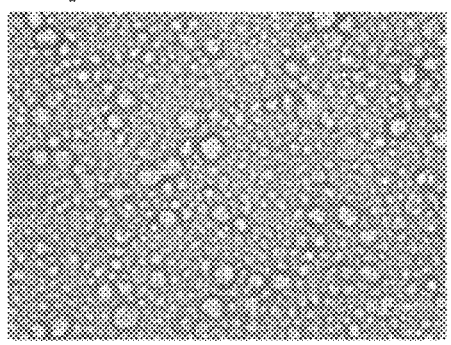  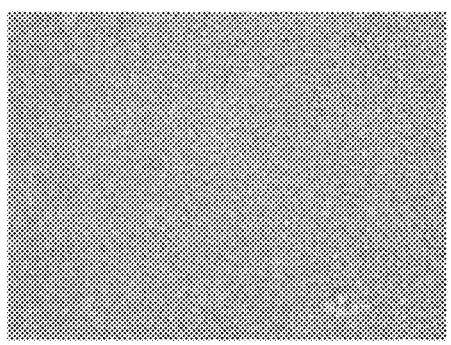
Non-neutralized
After neutralization
Emulsion particle size : ~3(5)μm
Viscosity : 44690mPa·s
pH: 6.81
Example C (OLB)
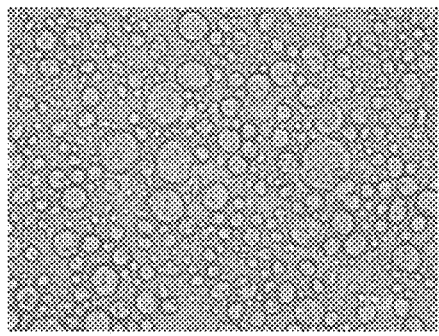  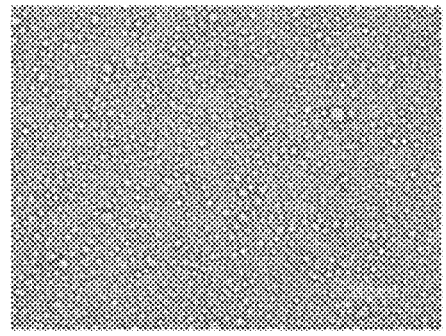
Non-neutralized
After neutralization
Emulsion particle size : ~5(10)μm
Viscosity : 9948mPa·s
pH: 7.32
Fig. 11

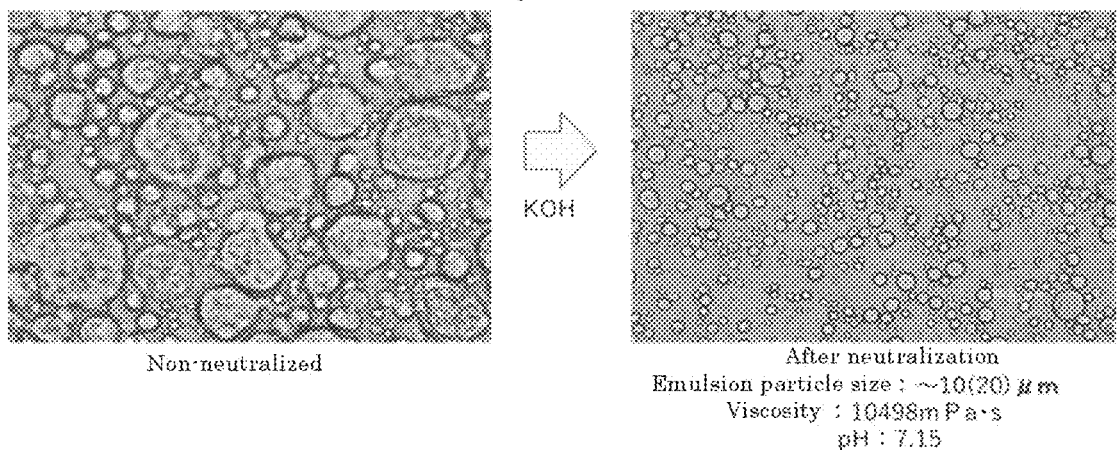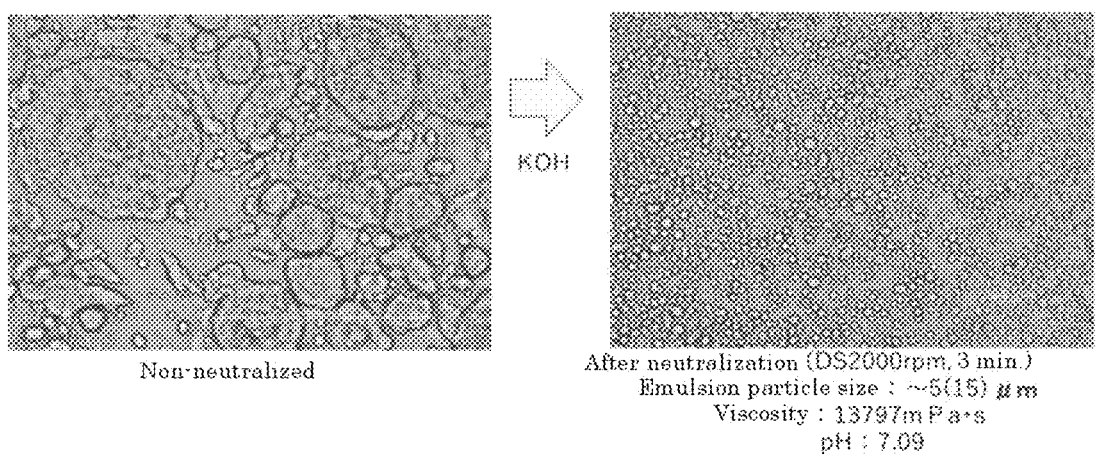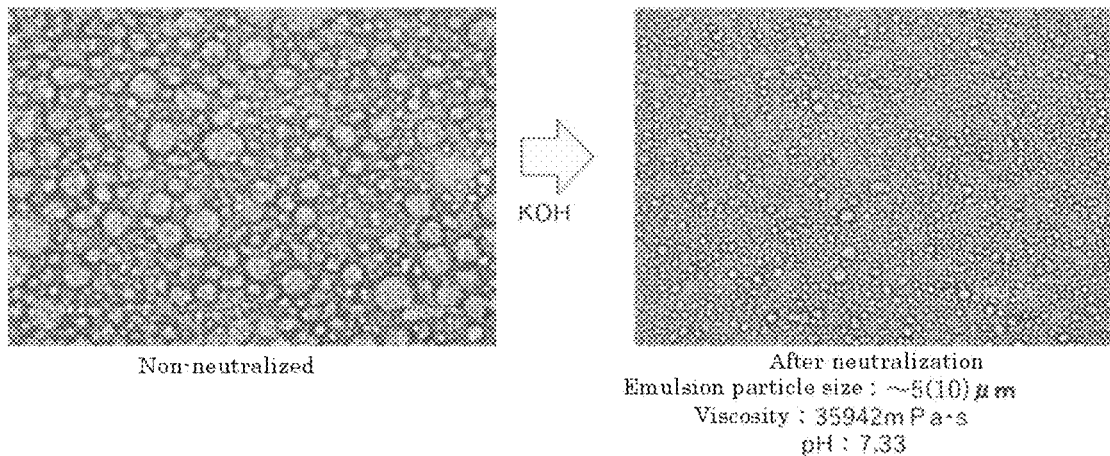
Fig. 12

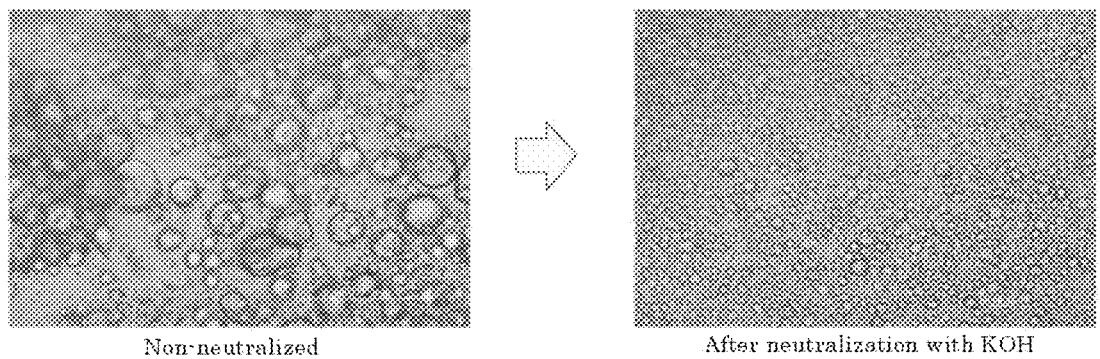
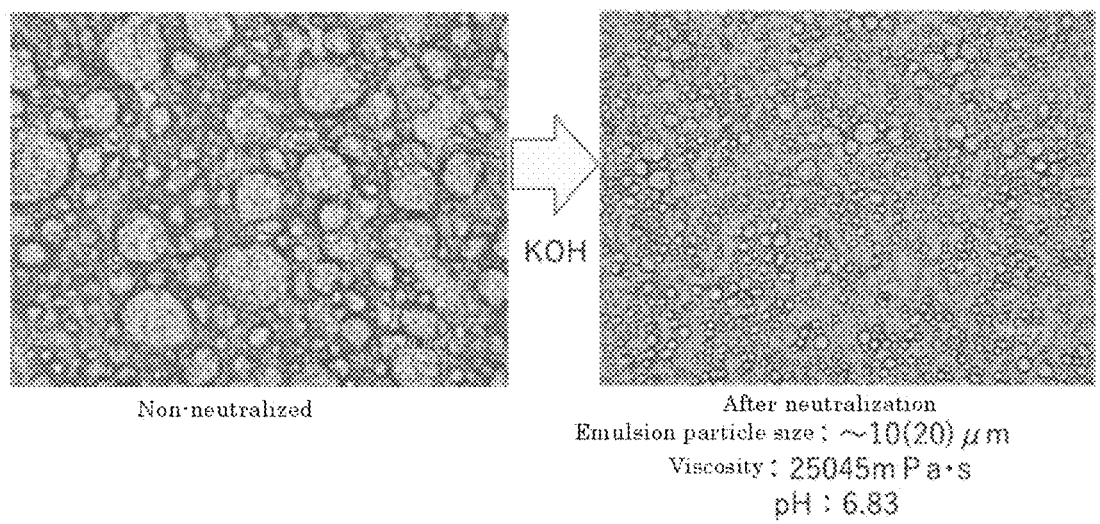
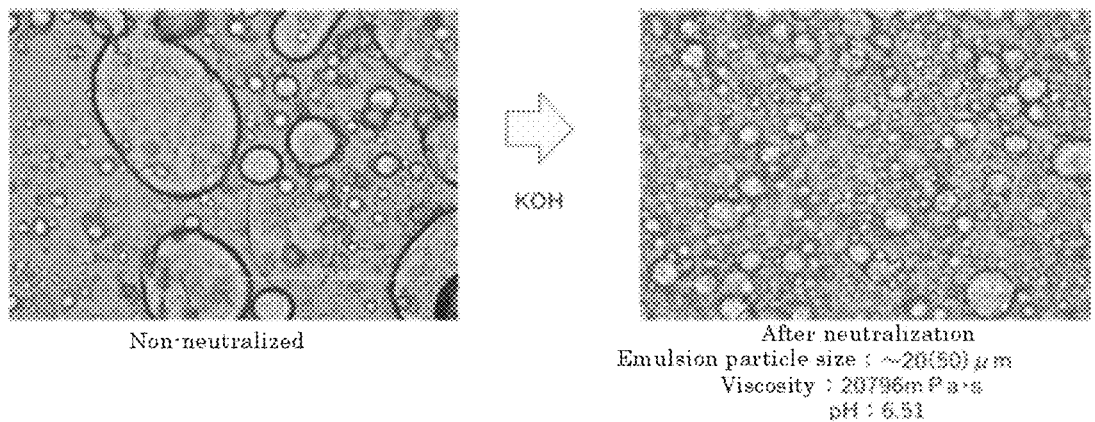
Fig. 13

| | Post-addition | Pre-addition |
|---|---|---|
| Example D | 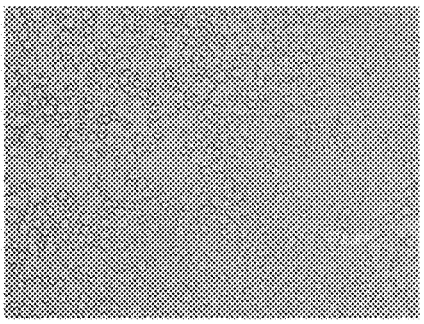 | 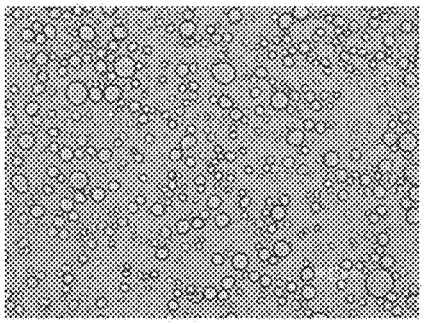 |
| Example E | 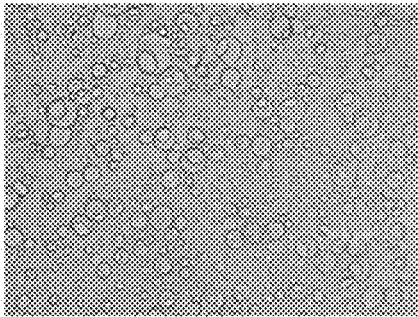 | 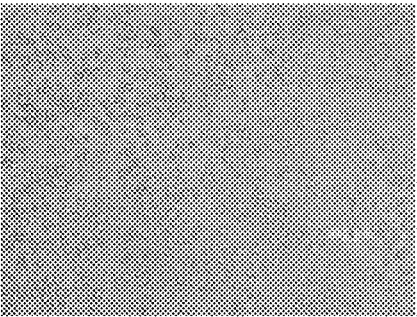 |
| Example F | 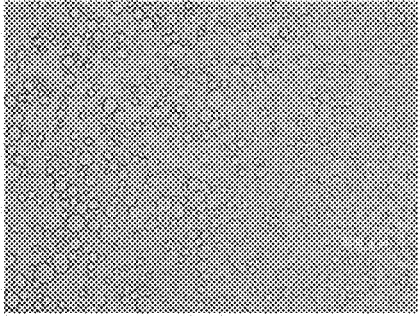 | 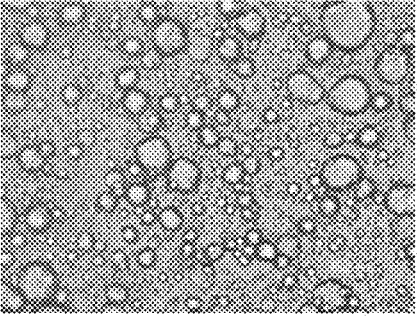 |
| Example G | 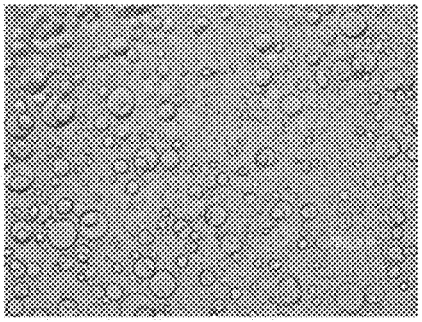 | 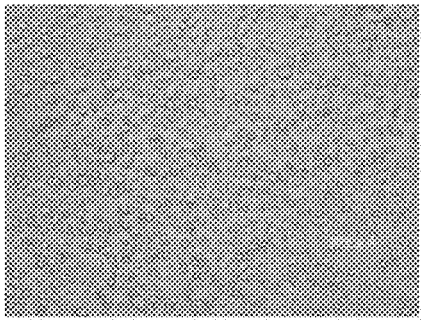 |
Fig. 19

COMPLEX AND EMULSION COMPOSITION

TECHNICAL FIELD

The present invention relates to a novel complex having emulsifying properties and an emulsion composition.

BACKGROUND ART

In general, when preparing an emulsion, a nonionic surfactant or an ionic surfactant is used as an emulsifier. However, since oils to be emulsified show various polarities, in order to obtain a stable emulsion, the degree of polarity of the oil, that is, the required HLB, is first obtained, and the above surfactant is selected and used accordingly. In many cases, as an emulsifier, a combination of a hydrophilic emulsifier having a high HLB and a lipophilic emulsifier having a low HLB is used.

Examples of hydrophilic emulsifiers having a high HLB include, for example, anionic surfactants such as fatty acid soap and alkyl sulfate ester salts; cationic surfactants such as distearyl dimethyl ammonium chloride and stearyl trimethyl ammonium chloride; and nonionic surfactants such as polyoxyethylene alkyl ethers, polyoxyethylene fatty acid esters and polyoxyethylene sorbitan fatty acid esters having a polyoxyethylene chain with long chain length.

Examples of lipophilic emulsifiers having a low HLB include, for example, nonionic surfactants having a short polyoxyethylene chain length, and nonionic surfactants such as sorbitan fatty acid esters and glycerin fatty acid esters, etc.

The required HLB of an oil to be emulsified is obtained by using a nonionic surfactant wherein HLB has been already known, and conventionally, this has required very complicated means such as changing the amount ratio of high HLB surfactant and low HLB surfactant. Then, an emulsion is prepared by selecting an emulsifier on the basis of the obtained required HLB; however, in fact a stable emulsion is rarely obtained, and there has been a problem that the experiment has to be repeated in a trial and error-like manner.

To solve such a problem, it is disclosed that an emulsifier containing an alkanolamide of oleic acid and an anionic surfactant can exert an emulsifying power for a relatively wide range of required HLB (Patent Document 1). However, the emulsion composition using this surfactant has a problem of high irritation to the skin.

In addition, a novel complex consisting of an amphoteric surfactant and/or a semipolar surfactant (hereinafter referred to as amphoteric surfactant) and a higher fatty acid has been proposed; however, the odor of oxidative degradation of higher fatty acids becomes a problem, and in terms of usability, since an active agent is used, stickiness derived from the active agent is generated; and this novel complex is not actually put into practical use as a basic skeleton of preparations (Patent Document 2).

In the end, an emulsifier capable of exerting excellent emulsifying power even on oils having a wide range of required HLB, and capable of achieving both stability and usability have not yet been obtained.

Incidentally, a secondary amide including an amide alcohol has been studied as an agent imparting moisture resistance, and in a composition using this, formulation wherein a secondary amide is used together with a hydrophilic acrylic polymer (a carboxyl group-containing polymer) as a thickener has been prepared (Patent Document 3). However, according to the preparation method described in this document, no complex is formed and the use of a common emulsifier (surfactant) is required for the preparation of an emulsion composition.

It has been proposed to mix polyethylene and N-erucyl-6-hydroxycaproamide to form a film (Patent Document 4). However, it is not a technique concerning the preparation of an emulsion.

It has also been proposed to prepare a silver halide color photographic light-sensitive material by mixing an alcohol including an amide alcohol with an aqueous gelatin solution comprising a surfactant to prepare an emulsion (Patent Document 5). However, it has not been proposed to carry out emulsification by using an amide alcohol and a carboxyl group-containing polymer.

CITATION LIST

Patent Document

[Patent Document 1] JP A S61-114724
[Patent Document 2] JP A H06-65596
[Patent Document 3] JP A H01-502116
[Patent Document 4] JP B S50-17216
[Patent Document 5] JP A H08-29934

DISCLOSURE OF INVENTION

Problems to be Solved by the Invention

In view of the above problems in the prior art, it is an object of the present invention to provide an emulsifier which exerts an excellent emulsifying power for oils having a wide range of required HLB. It is a further object of the present invention to provide an emulsion utilizing such emulsifying power. Another object of the present invention is to provide an emulsifier capable of obtaining an emulsion having excellent stability, and to provide a stable emulsion. It is a further object of the present invention to provide an emulsifier capable of providing an emulsion having excellent feeling of use, and to provide an emulsion having excellent feeling of use.

Means for Solving the Problems

During extensive research to solve the above problems, the present inventors have discovered that emulsification is possible by using an amide alcohol and a polymer containing a carboxyl group; and as a result of further research, the inventors have completed the present invention.

That is, the present invention relates to (1) to (12) below.
(1)
A method for producing an emulsion composition, wherein an aqueous phase containing a carboxyl group-containing polymer, and an oil phase containing an amide alcohol represented by formula (I):

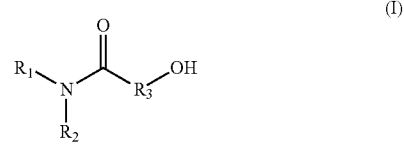

wherein
$R_1$ is a C6-C22 hydrocarbon group,
$R_2$ is H, or a C6-C22 hydrocarbon group, $R_3$ is a linear or branched C2-C21 hydrocarbon group, are mixed.

(2)

The method according to (1), which comprises neutralizing by adding a neutralizing agent.

(3)

A method according to (2), wherein the aqueous phase containing the carboxyl group-containing polymer is neutralized by adding a neutralizing agent, and the aqueous phase and the oil phase are mixed.

(4)

The method according to (2), wherein, after mixing the aqueous phase and the oil phase, the mixture is neutralized by adding a neutralizing agent.

(5)

The method according to any one of (1) to (4), wherein the carboxyl group-containing polymer has a molecular weight of 500,000 to 3,000,000 and a carboxyl group content of 50 to 70%.

(6)

The method according to any one of (1) to (5), wherein the carboxyl group-containing polymer is a carboxyvinyl polymer and/or an alkyl-modified carboxyvinyl polymer.

(7)

The method according to (6), wherein the carboxyl group-containing polymer is a carboxyvinyl polymer represented by formula (II):

$$-\!\!\left(\!CH\!-\!CH_2\!\right)_{\overline{n}}\!- \quad \text{(II)}$$
$$\qquad \ \ |$$
$$\qquad \ \ COOH$$

wherein n is an integer,
and/or an alkyl-modified carboxyvinyl polymer represented by formula (III):

$$-\!\!\left(\!CH\!-\!CH_2\!\right)_{\overline{x}}\!\!\left(\!\!\begin{array}{c}CH_3\\|\\C\\|\\COOR\end{array}\!\!-\!CH_2\!\right)_{\overline{y}}\!- \quad \text{(III)}$$
$$\quad \ |$$
$$\ COOH$$

wherein x and y are each independently an integer,
R is a C10-C30 alkyl group.

(8)

The method according to any one of (1) to (7), wherein the amide alcohol is an amide alcohol of formula (I), wherein
$R_1$ is a C10-C22 hydrocarbon group,
$R_2$ is H,
$R_3$ is a C3-C12 hydrocarbon group.

(9)

The method according to (8), wherein the amide alcohol is one or more selected from:

(I-1)

[structure]

(I-2)

[structure]

(I-3)

[structure]

(I-4)

[structure]

(10)

An emulsion composition obtained by the method according to any one of (1) to (9).

(11)

An agent containing an amide alcohol represented by formula (I):

$$\text{(I)}$$

[structure showing $R_1$, $R_2$, $R_3$, N, O, OH]

wherein
$R_1$ is a C6-C22 hydrocarbon group,
$R_2$ is H, or a C6-C22 hydrocarbon group,
$R_3$ is a linear or branched C2-C21 hydrocarbon group,
wherein the agent is used for emulsification by forming a complex with a carboxyl group-containing polymer.

(12)

An agent containing a carboxyl group-containing polymer, wherein the agent is used for emulsification by forming a complex with an amide alcohol represented by formula (I):

$$\text{(I)}$$

[structure showing $R_1$, $R_2$, $R_3$, N, O, OH]

wherein
$R_1$ is a C6-C22 hydrocarbon group,
$R_2$ is H, or a C6-C22 hydrocarbon group,
$R_3$ is a linear or branched C2-C21 hydrocarbon group.

Furthermore, the present invention relates to [1] to [14] below.

[1]

A complex wherein an amide alcohol represented by formula (I):

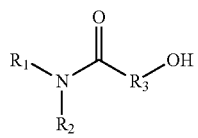
(I)

wherein
$R_1$ is a C6-C22 hydrocarbon group,
$R_2$ is H, or a C6-C22 hydrocarbon group,
$R_3$ is a linear or branched C2-C21 hydrocarbon group,
and a carboxyl group-containing polymer are bonded.

[2]
The complex according to [1] wherein the amide bond moiety of the amide alcohol and the carboxyl group moiety of the polymer are hydrogen-bonded.

[3]
The complex according to [1] or [2], wherein the carboxyl group-containing polymer is a carboxyvinyl polymer and/or an alkyl-modified carboxyvinyl polymer.

[4]
The complex according to any one of [1] to [3], wherein the carboxyl group-containing polymer is a carboxyvinyl polymer represented by formula (II):

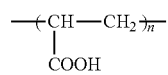
(II)

wherein n is an integer,
and/or an alkyl-modified carboxyvinyl polymer represented by formula (III):

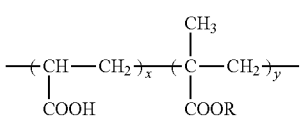
(III)

wherein x and y are each independently an integer,
R is a C10-C30 alkyl group.

[5]
The complex according to any one of [1] to [4], comprising an amide alcohol of formula (I), wherein
$R_1$ is a C10-C22 hydrocarbon group,
$R_2$ is H,
$R_3$ is a C3-C12 hydrocarbon group.

[6]
The complex according to any one of [1] to [5], wherein the amide alcohol is one or more selected from:

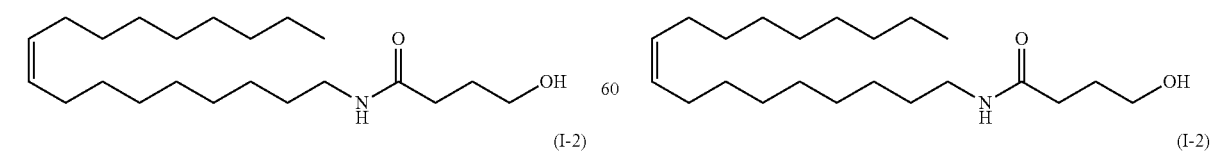

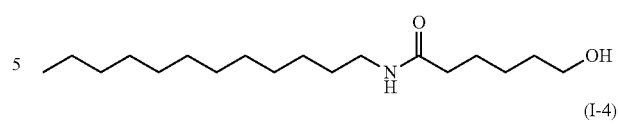
(I-3)

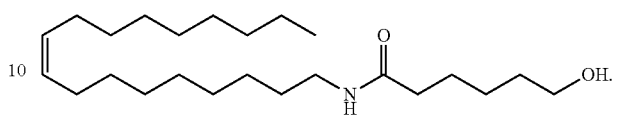
(I-4)

[7]
An O/W emulsion composition, which comprises an amide alcohol represented by formula (I):

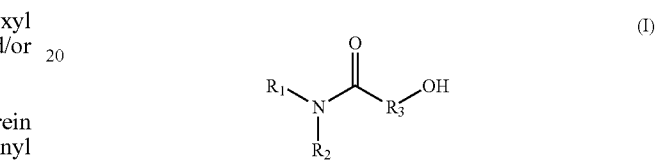
(I)

wherein
$R_1$ is a C6-C22 hydrocarbon group,
$R_2$ is H, or a C6-C22 hydrocarbon group,
$R_3$ is a linear or branched C2-C21 hydrocarbon group,
and a carboxyl group-containing polymer, and does not comprise a surfactant.

[8]
An O/W emulsion composition obtained by mixing an aqueous phase containing a carboxyl group-containing polymer and an oil phase containing an amide alcohol, and neutralizing the mixture by the addition of an alkali.

[9]
The O/W emulsion composition according to [7] or [8], wherein the carboxyl group-containing polymer is a carboxyvinyl polymer and/or an alkyl-modified carboxyvinyl polymer.

[10]
The O/W emulsion composition according to any one of [7] to [9], comprising an amide alcohol of formula (I) wherein
$R_1$ is a C10-C22 hydrocarbon group,
$R_2$ is H,
$R_3$ is a C3-C12 hydrocarbon group.

[11]
The O/W emulsion composition according to any one of [7] to [10], wherein the amide alcohol is one or more selected from:

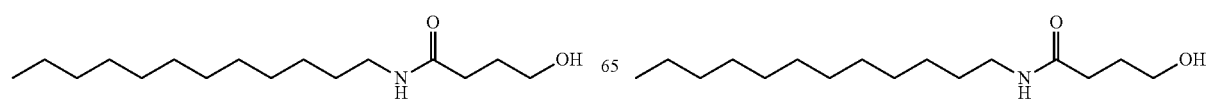

-continued (I-3)

~~~
         O
         ‖
   \/\/\/\/\/\/\/\N——⎞⎞⎞——OH
              H
~~~

(I-4)

~~~
              O
              ‖
\/\/\/=\/\/\/\/\/N——⎞⎞⎞——OH.
              H
~~~

[12]

The O/W emulsion composition according to any one of [7] to [11], comprising 0.1 to 10.0 mass % of the amide alcohol represented by formula (I) and 0.01 to 5.0 mass % of the carboxyl group-containing polymer.

[13]

The O/W emulsion composition according to any one of [7] to [12], wherein the pH is 6.0 to 9.0.

[14]

A method for producing an O/W emulsion composition, comprising mixing an aqueous phase containing a carboxyl group-containing polymer and an oil phase containing an amide alcohol, and neutralizing the mixture by the addition of an alkali.

The present invention further relates to [A1] to [A14] below.

[A1]

An agent containing an amide alcohol represented by formula (I):

$$\begin{array}{c} R_1 \diagdown_N \diagup^{O}\diagdown_{R_3}\diagup^{OH} \\ | \\ R_2 \end{array} \quad (I)$$

wherein
$R_1$ is a C6-C22 hydrocarbon group,
$R_2$ is H, or a C6-C22 hydrocarbon group,
$R_3$ is a linear or branched C2-C21 hydrocarbon group,
wherein the agent is used for O/W type emulsification by forming a complex with a carboxyl group-containing polymer which is a carboxyvinyl polymer and/or an alkyl-modified carboxyvinyl polymer.

[A2]

The agent according to [A1], wherein the carboxyl group-containing polymer is a carboxyvinyl polymer represented by formula (II):

$$-(CH-CH_2)_n- \atop | \atop COOH \quad (II)$$

wherein n is an integer,
and/or an alkyl-modified carboxyvinyl polymer represented by formula (III):

$$-(CH-CH_2)_x-(C(CH_3)-CH_2)_y- \atop | \qquad\qquad | \atop COOH \qquad\quad COOR \quad (III)$$

wherein x and y are each independently an integer,
R is a C10-C30 alkyl group.

[A3]

The agent according to [A1] or [A2], comprising an amide alcohol of formula (I) wherein
$R_1$ is a C10-C22 hydrocarbon group,
$R_2$ is H,
$R_3$ is a C3-C12 hydrocarbon group.

[A4]

The agent according to any one of [A1] to [A3], wherein the amide alcohol is one or more selected from:

(I-1)

~~~
              O
              ‖
\/\/\/=\/\/\/\/\/N——⎞——OH
              H
~~~

(I-2)

~~~
         O
         ‖
   \/\/\/\/\/\/\/\N——⎞——OH
              H
~~~

(I-3)

~~~
         O
         ‖
   \/\/\/\/\/\/\/\N——⎞⎞⎞——OH
              H
~~~

(I-4)

~~~
              O
              ‖
\/\/\/=\/\/\/\/\/N——⎞⎞⎞——OH.
              H
~~~

[A5]

An O/W emulsion composition, which comprises an amide alcohol represented by formula (I):

$$\begin{array}{c} R_1 \diagdown_N \diagup^{O}\diagdown_{R_3}\diagup^{OH} \\ | \\ R_2 \end{array} \quad (I)$$

wherein
$R_1$ is a C6-C22 hydrocarbon group,
$R_2$ is H, or a C6-C22 hydrocarbon group,
$R_3$ is a linear or branched C2-C21 hydrocarbon group,
and a carboxyl group-containing polymer, and does not comprise a surfactant.

[A6]

An O/W emulsion composition, which is obtained by mixing an aqueous phase containing a carboxyl group-containing polymer and an oil phase containing an amide alcohol represented by formula (I):

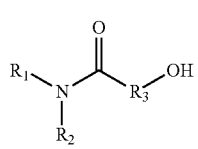
(I)

wherein
$R_1$ is a C6-C22 hydrocarbon group,
$R_2$ is H, or a C6-C22 hydrocarbon group,
$R_3$ is a linear or branched C2-C21 hydrocarbon group,
and by neutralizing the resulting mixture by the addition of an alkali.

[A7]
The O/W emulsion composition according to [A6], wherein the carboxyl group-containing polymer is a carboxyvinyl polymer and/or an alkyl-modified carboxyvinyl polymer.

[A8]
The O/W emulsion composition according to [A5] or [A6], comprising an amide alcohol of formula (I) wherein
$R_1$ is a C10-C22 hydrocarbon group,
$R_2$ is H,
$R_3$ is a C3-C12 hydrocarbon group.

[A9]
The O/W emulsion composition according to any one of [A5] to [A8], wherein the amide alcohol is one or more selected from:

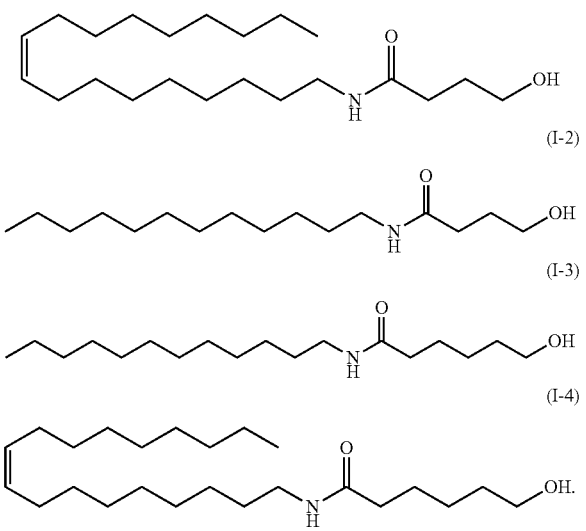

[A10]
The O/W emulsion composition according to any one of [A5] to [A9], comprising 0.1 to 10.0 mass % of the amide alcohol represented by formula (I) and 0.01 to 5.0 mass % of the carboxyl group-containing polymer.

[A11]
The O/W emulsion composition according to any one of [A5] to [A10], wherein the pH is 6.0 to 9.0.

[A12]
A method for producing an O/W emulsion composition, which comprises mixing an aqueous phase containing a carboxyl group-containing polymer and an oil phase containing an amide alcohol represented by formula (I):

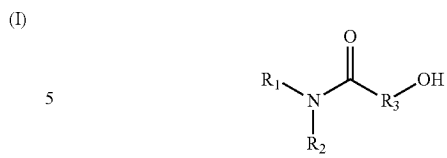
(I)

wherein
$R_1$ is a C6-C22 hydrocarbon group,
$R_2$ is H, or a C6-C22 hydrocarbon group,
$R_3$ is a linear or branched C2-C21 hydrocarbon group,
and neutralizing the resulting mixture by the addition of an alkali.

[A13]
A complex having a carboxylate ion, formed by bonding an amide alcohol represented by formula (I):

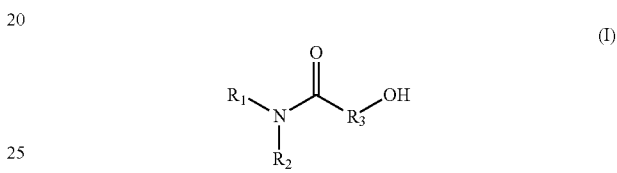
(I)

wherein
$R_1$ is a C6-C22 hydrocarbon group,
$R_2$ is H, or a C6-C22 hydrocarbon group,
$R_3$ is a linear or branched C2-C21 hydrocarbon group,
and a carboxyl group-containing polymer which is a carboxyvinyl polymer and/or an alkyl-modified carboxyvinyl polymer.

[A14]
The complex according to [A13], wherein the carboxyl group-containing polymer is a carboxyvinyl polymer represented by formula (II):

(II)

wherein n is an integer,
and/or an alkyl-modified carboxyvinyl polymer represented by formula (III):

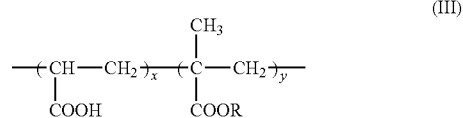
(III)

wherein x and y are each independently an integer,
R is a C10-C30 alkyl group.

Advantageous Effects of Invention

The present invention provides a novel complex that can be used as an emulsifier. The complex of the present invention exerts an excellent emulsifying power such as oil-in-water type emulsification, water-in-oil type emulsification for oils having a wide range of required HLB. In addition, the complex of the present invention can provide an emulsion excellent in stability. Furthermore, the present invention can provide a stable emulsion without using a surfactant.

BRIEF DESCRIPTION OF DRAWINGS

FIG. 3 is a graph showing FT-IR measurement results of amide alcohol, carbomer, and blended preparation (neutralized).

FIG. 7 is a diagram showing the structure of the thickener used in comparative formulation 6, and an emulsified state of comparative formulation 6.

FIG. 8 is a diagram showing an emulsified state of comparative formulation 6 and comparative formulation 7.

FIG. 9 is a diagram showing an emulsified state of the basic formulation 2 before neutralization and after neutralization.

FIG. 10 is a diagram showing an emulsified state of Example 3 and comparative formulation 8 before neutralization and after neutralization.

FIG. 11 is a diagram showing an emulsified state of Examples A, B and C before neutralization and after neutralization.

FIG. 12 is a diagram showing an emulsified state of Examples 4, 8 and 13 before neutralization and after neutralization.

FIG. 13 is a diagram showing an emulsified state of Examples 14, 19 and 20 before neutralization and after neutralization.

FIG. 19 is a diagram showing an emulsified state in terms of pre-addition and post-addition in Examples D to G.

EMBODIMENTS FOR CARRYING OUT THE INVENTION

Component (A): Amide Alcohol

Figure 1:
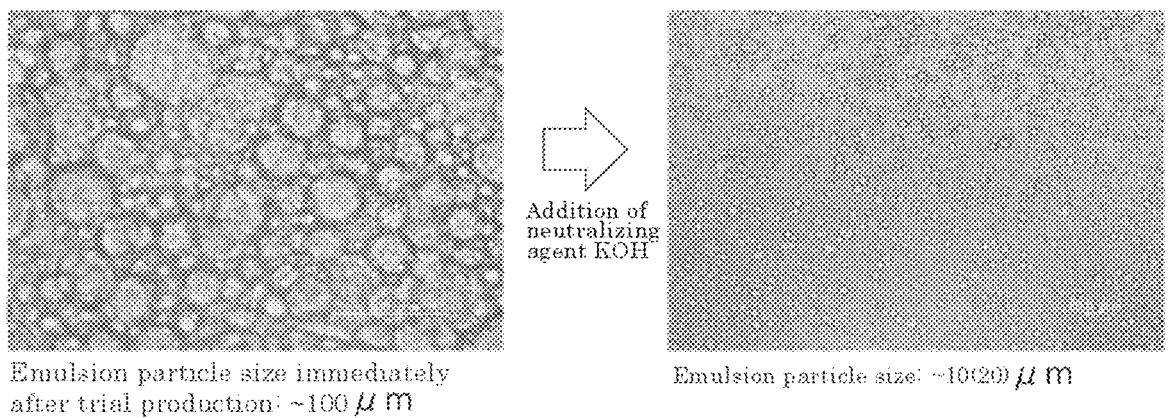
FIG. 1 is a diagram showing an emulsified state of basic formulation before neutralization and after neutralization.

The amide alcohol used in the present invention is represented by the following formula (I):

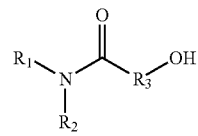

wherein
$R_1$ is a C6-C22 hydrocarbon group,
$R_2$ is H, or a C6-C22 hydrocarbon group,
$R_3$ is a linear or branched C2-C21 hydrocarbon group.

In one embodiment of the present invention, an amide alcohol of formula (I) wherein $R_1$ is a C10-C22 hydrocarbon group, $R_2$ is H, and $R_3$ is a C3-C12 hydrocarbon group is preferred, and an amide alcohol of formula (I) wherein $R_1$ is a C12-C18 hydrocarbon group, $R_2$ is H, and $R_3$ is a C3-C5 hydrocarbon group is particularly preferred.

In another embodiment of the present invention, an amide alcohol of formula (I), wherein $R_1$ is a linear or branched unsaturated C10-C22 hydrocarbon group; or a cyclic C6-C22 hydrocarbon group; or a benzyl group or phenylethyl group, is preferred.

In a preferred embodiment of the present invention, the amide alcohol of formula (I) has a structure of formulas (I-1) to (I-4) below:

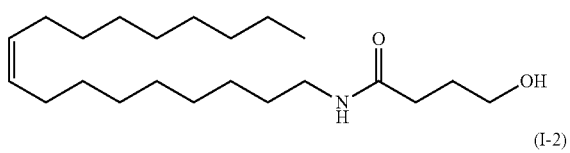

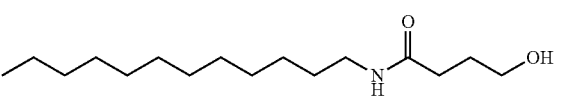

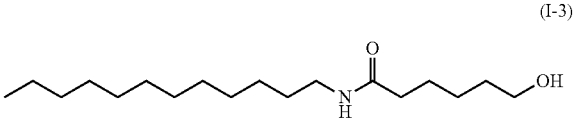

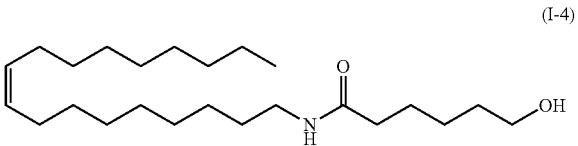 [SMILES: CCCCCCCC/C=C\CCCCCCCCNC(=O)CCCCCO]

As used herein, the term "hydrocarbon group" may be saturated or unsaturated, linear or branched or cyclic, or a combination of linear or branched with cyclic, unless otherwise specified, and includes a hydrocarbon group consisting of a linear or branched hydrocarbon moiety such as benzyl group, phenylethyl group and a cyclic hydrocarbon moiety.

That is, the C6-C22 hydrocarbon group in $R_1$ and $R_2$ includes a linear, branched or cyclic C6-C22 hydrocarbon group, or a C6-C22 hydrocarbon group consisting of a linear or branched hydrocarbon moiety and a cyclic hydrocarbon moiety, and examples thereof include cyclic groups such as cyclohexyl, decahydronaphthyl, tetrahydrodicyclopentadiene, sterol, phenyl, naphthyl, anthracenyl; branched alkyl groups such as ethylhexyl, isostearyl, octyldodecyl; multi-branched alkyl groups such as dimethyl, trimethyl, tetramethyl; linear alkyl groups such as hexyl, octyl, lauryl, myristyl, cetyl, stearyl, arachyl, behenyl; and alkenyl groups such as oleyl and elaidyl.

In one embodiment of the invention, $R_1$ is preferably cyclohexyl, ethylhexyl, octyl, lauryl, myristyl, stearyl, oleyl, benzyl or phenylethyl, with lauryl and oleyl being particularly preferred.

In one embodiment of the present invention, $R_2$ is preferably H.

The hydrocarbon group in $R_3$ is a linear or branched C2-C21 hydrocarbon group having no cyclic structure, and examples thereof include alkyl groups such as propyl, butyl, pentyl, hexyl, heptyl, octyl, ethylhexyl, and alkenyl groups such as butylene, pentylene, hexylene, heptylene.

In one embodiment of the present invention, $R_3$ is preferably propylene, butylene, pentylene or hexylene.

Amide alcohols can be prepared using known synthetic methods.

Examples include:
aminolysis reaction of acid chloride and amine (Schotten-Baumann reaction),
aminolysis reaction of anhydrous fatty acid and amine,
aminolysis reaction of methyl ester and amine,
aminolysis reaction of fatty acid and amine,
aminolysis reaction of lactone and amine,
and the like.

Specifically, for example, it can be synthesized by a method described in Japanese Patent Application No. 2016-114276 (JP 6247340 B, registered on Nov. 24, 2017 and published on Dec. 13, 2017).

Component (B): Carboxyl Group-Containing Polymer

The carboxyl group-containing polymer used in the present invention is not particularly limited as long as it is a polymer having a carboxyl group in the molecule. From the viewpoint of providing appropriate emulsifying ability, typically, those having a molecular weight of 500,000 to 3,000,000 and a carboxyl group content of approximately 50 to 70% are preferred.

The carboxyl group-containing polymer becomes water-soluble by neutralization with an alkaline substance, and it is generally used as a thickener.

Examples of carboxyl group-containing polymer include carboxyvinyl polymer, and alkyl-modified carboxyvinyl polymers such as alkyl acrylate/methacrylate copolymer, etc., acrylic polymers such as alkyl acrylate/alkyl methacrylate polyoxyethylene ester copolymer, alkyl acrylate/alkyl itaconate polyoxyethylene ester copolymer, steareth-10 allyl ether/alkyl acrylate copolymer, etc., and non-acrylic polymers such as methyl vinyl ether/maleic anhydride/decadiene copolymer, etc. As the carboxyl group-containing polymer, carboxyvinyl polymers and alkyl-modified carboxyvinyl polymers are particularly preferred.

In one embodiment of the present invention, the carboxyl group-containing polymer is not gelatin.

A carboxyvinyl polymer, also called carbomer (INCI name: Carbomer), is a polymer having a structure represented by the following formula (II):

(II)

wherein
n is an integer, which is typically from 40 to 100.

Specifically, examples include carboxyvinyl polymers commercially available under the following trade name:
Acritamer 934 (Rita Corporation)
Acritamer 940 (Rita Corporation)
Acritamer 941 (Rita Corporation)
Acritamer 990 (Rita Corporation)
Acritamer 501E (Rita Corporation)
Acritamer 504E (Rita Corporation)
Acritamer 505E (Rita Corporation)
AEC Carbomer 940 (A & E Connock (Perfumery & Cosmetics) Ltd.)
Aqupec HV-501 (Sumitomo Seika Chemicals Co., Ltd.)
Aqupec HV-504 (Sumitomo Seika Chemicals Co., Ltd.)
Aqupec HV-505 (Sumitomo Seika Chemicals Co., Ltd.)
Aqupec HV-501E (Sumitomo Seika Chemicals Co., Ltd.)
Aqupec HV-504E (Sumitomo Seika Chemicals Co., Ltd.)
Aqupec HV-505E (Sumitomo Seika Chemicals Co., Ltd.)
Aqupec HV-801E (Sumitomo Seika Chemicals Co., Ltd.)
Aqupec HV-805E (Sumitomo Seika Chemicals Co., Ltd.)
Aqupec HV-505ED (Sumitomo Seika Chemicals Co., Ltd.)
Aqupec HV-801EG (Sumitomo Seika Chemicals Co., Ltd.)
Aqupec HV-805EG (Sumitomo Seika Chemicals Co., Ltd.)
Carbopol Clear Polymer (Lubrizol Advanced Materials, Inc.)
Carbopol ETD 2050 Polymer (Lubrizol Advanced Materials, Inc.)
Carbopol 934 Polymer (Lubrizol Advanced Materials, Inc.)
Carbopol 940 Polymer (Lubrizol Advanced Materials, Inc.)
Carbopol 941 Polymer (Lubrizol Advanced Materials, Inc.)
Carbopol 980 Polymer (Lubrizol Advanced Materials, Inc.)
Carbopol 981 Polymer (Lubrizol Advanced Materials, Inc.)
Carbopol 2984 Polymer (Lubrizol Advanced Materials, Inc.)
Carbopol 5984 Polymer (Lubrizol Advanced Materials, Inc.)
Carbopol Ultrez 10 Polymer (Lubrizol Advanced Materials, Inc.)
Carbopol Ultrez 30 Polymer (Lubrizol Advanced Materials, Inc.)
CustoPoly J 100 (Custom Ingredients, Inc.)
CustoPoly J 300 (Custom Ingredients, Inc.)
CustoPoly J 400 (Custom Ingredients, Inc.)
Easygel DO (3V Sigma USA Inc.)
Flogel 700 (SNF SAS)
Flogel 1000 (SNF SAS)
Junlon PW-110 (Nihon Junyaku Company, Ltd.)
Junlon PW-111 (Nihon Junyaku Company, Ltd.)
Junlon PW-302S (Nihon Junyaku Company, Ltd.)
Polacril 40 (Lehvoss Italia s.r.l.)
Polygel CA (3V Sigma USA Inc.)
Polygel CB (3V Sigma USA Inc.)
Polygel CS (3V Sigma USA Inc.)
Polygel DV (3V Sigma USA Inc.)
Polygel TG (3V Sigma USA Inc.)
SuperGel CE (Sino Lion USA)
Synthalen K (3V Sigma USA Inc.)
Synthalen L (3V Sigma USA Inc.)
Synthalen M (3V Sigma USA Inc.)
Tego Carbomer 134 (Evonik Nutrition & Care GmbH)
Tego Carbomer 140 (Evonik Nutrition & Care GmbH)
Tego Carbomer 141 (Evonik Nutrition & Care GmbH)
Tego Carbomer 340 FD (Evonik Nutrition & Care GmbH).

The alkyl-modified carboxyvinyl polymer is a copolymer of acrylic acid and/or methacrylic acid with alkyl acrylate and/or alkyl methacrylate thereof.

Specific examples of alkyl-modified carboxyvinyl polymer include (acrylates/alkyl acrylates (C10-30)) cross polymer (INCI name: Acrylates/C10-30 Alkyl Acrylates Cross polymer, also called alkyl acrylate/methacrylate copolymer), which is a polymer having a structure represented by the following formula (III):

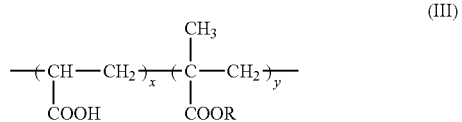

wherein
R is a C10-30 alkyl group,
x and y are integers, each of which can be arbitrarily selected from integers of 1 or more, and typically x+y=40 to 100, and when y is 2 or more, R may be the same or different.

Specifically, the examples include alkyl-modified carboxyvinyl polymers commercially available under the following trade name:
Acritamer 501ED (Rita Corporation)
Acritamer 505ED (Rita Corporation)
Aqupec HV-701EDR (Sumitomo Seika Chemicals Co., Ltd.)
Aqupec HV-501ER (Sumitomo Seika Chemicals Co., Ltd.)
Aqupec SER W-150C (Sumitomo Seika Chemicals Co., Ltd.)
Aqupec SER W-300C (Sumitomo Seika Chemicals Co., Ltd.)
Carbopol ETD 2020 Polymer (Lubrizol Advanced Materials, Inc.)
Carbopol 1342 Polymer (Lubrizol Advanced Materials, Inc.)
Carbopol 1382 Polymer (Lubrizol Advanced Materials, Inc.)
Carbopol SC 200 (Lubrizol Advanced Materials, Inc.)
Carbopol SC 500 Polymer (Lubrizol Advanced Materials, Inc.)
Carbopol Ultrez 20 Polymer (Lubrizol Advanced Materials, Inc.)
Carbopol Ultrez 21 Polymer (Lubrizol Advanced Materials, Inc.)
Carbopol Xtra-11 Polymer (Lubrizol Advanced Materials, Inc.)
Pemulen EZ-4U Polymeric Emulsifier (Lubrizol Advanced Materials, Inc.)
Pemulen TR-1 Polymer (Lubrizol Advanced Materials, Inc.)
Pemulen TR-2 Polymer (Lubrizol Advanced Materials, Inc.)
Tego Carbomer 341 ER (Evonik Nutrition & Care GmbH)
TEGO Carbomer 750 HD (Evonik Nutrition & Care GmbH).

"Complex" in the present invention means a complex formed from an amide alcohol and a carboxyl group-containing polymer.

The complex can be formed by mixing a carboxyl group-containing polymer and an amide alcohol. By neutralizing such a mixture with an alkali, a complex having a higher emulsifying ability can be formed.

In one embodiment of the present invention, the complex can be formed by adding an amide alcohol to an aqueous solution of a carboxyl group-containing polymer, and then neutralizing with an alkali.

In another embodiment of the present invention, the complex can be formed by adding a carboxyl group-containing polymer to an oil phase containing an amide alcohol, and then neutralizing with an alkali.

In yet another embodiment of the present invention, the complex can be formed by adding an aqueous phase comprising a carboxyl group-containing polymer and an alkali to an oil phase containing an amide alcohol.

In yet another embodiment of the present invention, the complex can be formed by adding an amide alcohol to an aqueous solution comprising a carboxyl group-containing polymer and an alkali.

It is considered that the amide bond portion of the amide alcohol and the carbonyl group of the polymer form a hydrogen bond, and a part of the carboxyl group becomes COO and has hydrophilicity, thereby exerting emulsifying ability.

Thus, while not being bound by any theory, it is believed that the complex of the present invention forms a complex by bonding, more specifically hydrogen bonding of the amide bond moiety of the amide alcohol and the carbonyl group of the polymer.

In the present invention, "emulsion" means a composition prepared by emulsifying an oil phase comprising an oily component and an aqueous phase comprising an aqueous component, and includes an O/W emulsion, a W/O emulsion, etc.

In the present invention, the "O/W emulsion" is an oil-in-water emulsion, that is, an emulsion in which an oily component is dispersed in a continuous phase comprising an aqueous component.

In the present invention, the "W/O emulsion" is a water-in-oil emulsion, that is, an emulsion in which an aqueous component is dispersed in a continuous phase comprising an oily component.

The O/W emulsion can be prepared by dispersing an oil phase comprising an amide alcohol in an aqueous phase comprising a carboxyl group-containing polymer. When such an emulsion is neutralized with an alkali, a more stable emulsion having finer oil droplets can be prepared.

In one embodiment of the present invention, the O/W emulsion can be prepared by dispersing an oil phase comprising an amide alcohol in an aqueous phase comprising a carboxyl group-containing polymer, and neutralizing with an alkali.

In another embodiment of the present invention, the O/W emulsion can be prepared by dispersing an oil phase comprising an amide alcohol in an aqueous phase comprising a carboxyl group-containing polymer and an alkali.

In one embodiment of the present invention, emulsions such as O/W emulsion and W/O emulsion can be used for all purposes, but typically, they can be used for external preparations such as pharmaceuticals, quasi drugs, and cosmetics.

Emulsions such as O/W emulsion and W/O emulsion of the present invention can be used for various forms of products including pharmaceuticals such as external skin preparation comprising a drug; quasi drugs such as medicated cosmetics; skin care cosmetics such as gel lotion, milky lotion, cream, beauty essence, sunscreen, and daytime moisturizer; makeup cosmetics such as foundation, makeup base, eye shadow, mascara, as well as hair care cosmetics such as hair treatment, etc.

<Oily Component>

The oily component used in the emulsion such as O/W emulsion, W/O emulsion of the present invention is not particularly limited as long as it is a component generally used for cosmetics and the like; and examples thereof include oil agents such as animal and vegetable fats and oils, hydrocarbon oils, higher fatty acids, higher alcohols, ester oils, silicone oils, which can be used alone or in combination of two or more kinds.

Examples of animal and vegetable fats and oils or hydrogenated animal and vegetable fats and oils include avocado oil, eno oil, olive oil, cacao butter, kaya oil, apricot kernel oil, hydrogenated oil, wheat germ oil, sesame oil, rice germ oil, rice bran oil, sugar cane wax, *Camellia sinensis* leaf oil, safflower oil, Chinese tung oil, cinnamon oil, soybean oil, tea seed oil, *camellia* oil, evening primrose oil, corn oil, rapeseed oil, germ oil, palm oil, palm kernel oil, castor oil, hydrogenated castor oil, sunflower oil, grape oil, jojoba oil, macadamia nut oil, beeswax, cottonseed oil, cotton wax, Japan wax, montan wax, coconut oil, hydrogenated coconut oil, peanut oil, lanolin, liquid lanolin, reduced lanolin, lanolin alcohol, hard lanolin, lanolin acetate, lanolin fatty acid isopropyl ester, hexyl laurate, etc.

Examples of hydrocarbon oils include ozokerite, squalane, squalene, ceresin, paraffin, isoparaffin, paraffin wax, liquid paraffin (mineral oil), pristane, polyisobutylene, polyisobutene, hydrogenated polyisobutene, microcrystalline wax, polyethylene wax, vaseline, etc.

Examples of higher fatty acids include lauric acid, myristic acid, palmitic acid, stearic acid, isostearic acid, oleic acid, behenic acid, undecylenic acid, oleic acid, linoleic acid, linolenic acid, arachidonic acid, eicosapentaenoic acid (EPA), docosahexaenoic acid (DHA), isostearic acid, etc.

Examples of higher alcohols include myristyl alcohol, cetanol, stearyl alcohol, arachidyl alcohol, behenyl alcohol, hydrogenated rapeseed oil alcohol, etc.

Examples of ester oils include, as monoester, isononanoic acid esters such as isononyl isononanoate, isotridecyl isononanoate; 2-ethylhexanoic acids such as cetyl ethylhexanoate, hexyldecyl ethylhexanoate; myristic acid esters such as isopropyl myristate, isocetyl myristate, octyldodecyl myristate; isostearic acid esters such as ethyl isostearate, isopropyl isostearate, hexyldecyl isostearate, isostearyl isostearate, cholesteryl isostearate, phytosteryl isostearate; lactic acid esters such as isostearyl lactate, octyldodecyl lactate; oleic acid esters such as oleyl oleate, phytosteryl oleate, octyldodecyl oleate; neopentanoic acid esters such as isodecyl neopentanoate, isostearyl neopentanoate; palmitic acid esters such as isopropyl palmitate, ethylhexyl palmitate; and others such as octyldodecyl neodecanoate, octyldodecyl ricinoleate, oleyl erucate, octyldodecyl erucate, isopropyl lauroyl sarcosinate.

Examples of diester oils include diisobutyl adipate, diisopropyl adipate, diethylhexyl succinate, neopentyl glycol diisononanoate, neopentyl glycol diethylhexanoate, neopentyl glycol dicaprate, diisostearyl malate, diisopropyl dilinoleate, ethylene glycol dioctanoate, octyldodecyl stearoyl oxystearate, diisopropyl sebacate, di(cholesteryl/octyldodecyl) lauroyl glutamate, di(phytosteryl/octyldodecyl) lauroyl glutamate, etc.

Examples of triester oils include triethylhexanoin, trimethylolpropane triethylhexanoate, glyceryl tri(caprylate/caprate), triisostearin, trimethylolpropane triisostearate, etc.

Examples of tetraester oils include pentaerythrityl tetraethylhexanoate, pentaerythrityl tetraisostearate, etc.

Examples of polyester oils include polyglyceryl fatty acid esters such as polyglyceryl-2 isostearate, polyglyceryl-2 diisostearate, polyglyceryl-2 triisostearate, polyglyceryl-2 tetraisostearate.

Examples of highly viscous ester oils include hydrogenated castor oil isostearate, hydrogenated castor oil dimer dilinoleate, (polyglyceryl-2 isostearate/dimer dilinoleate) copolymer, (phytosteryl/isostearyl/cetyl/stearyl/behenyl) dimer dilinoleate, dimer dilinoleyl bis(phytosteryl/behenyl/isostearyl) dimer dilinoleate, di(isostearyl/phytosteryl) dimer dilinoleate, dimer dilinoleyl hydrogenated rosin condensate, dimer dilinoleyl diisostearate, dimer dilinoleyl dimer dilinoleate, di(cholesteryl/behenyl/octyldodecyl) lauroylglutamate, di(octyldodecyl/phytosteryl/behenyl) lauroylglutamate, myristoylmethylalanine (phytosteryl/decyltetradecyl), etc.

Examples of silicone oils include dimethylpolysiloxane, methylphenylpolysiloxane, alkyl-modified organopolysiloxane, terminal modified organopolysiloxane, fluorine-modified organopolysiloxane, amodimethicone, amino-modified organopolysiloxane, volatile silicone, alkyl dimethicone, cyclopentasiloxane, etc.

In one embodiment of the present invention, the blending amount of the oily component in the O/W emulsion is not particularly limited; from the viewpoint of usability, it may be 1.0 to 30.0 mass %, preferably 2.0 to 20.0 mass %, and more preferably 5.0 to 15.0 mass %.

In another embodiment of the present invention, the blending amount of the oily component in the W/O emulsion is not particularly limited; from the viewpoint of usability, it may be 30.0 to 80.0 mass %, preferably 40.0 to 70.0 mass %, and more preferably 50.0 to 60.0 mass %.

<Aqueous Component>

Aqueous components used in the emulsion such as O/W emulsion and W/O emulsion of the present invention are not particularly limited as long as they are components generally used in cosmetics and the like; and examples thereof include water such as purified water, ion exchanged water; and lower alcohols such as BG (1,3-butylene glycol), PG (propylene glycol), glycerin, ethanol, and these can be used alone or in combination of two or more kinds.

In one embodiment of the present invention, the blending amount of the aqueous component in the O/W emulsion is not particularly limited; from the viewpoint of usability, it may be 1.0 to 50.0 mass %, preferably 3.0 to 20.0 mass %, and more preferably 5.0 to 15.0 mass %.

In one embodiment of the present invention, the blending amount of the aqueous component in the W/O emulsion is not particularly limited; from the viewpoint of usability, it may be 10.0 to 70.0 mass %, preferably 15.0 to 65.0 mass %, and more preferably 20.0 to 60.0 mass %.

<Neutralizing Agent>

A neutralizing agent used for preparing the emulsion such as O/W emulsion and W/O emulsion of the present invention is not particularly limited as long as it is an alkaline component generally used in cosmetics and the like, and examples thereof include potassium hydroxide, triethanolamine, sodium hydroxide, basic amino acids such as L-arginine and L-lysine, 2-amino-2-methyl-1-propanol, etc., and these can be used alone or in combination of two or more kinds.

In addition, the neutralizing agent may be an active component such as tranexamic acid, carnosine.

The blending amount of the neutralizing agent can be appropriately selected depending on the type of the neutralizing agent and the composition of the whole emulsion; it is typically about 0.01 to 1.0 mass %.

<Surfactant>

In the present specification, the term "surfactant" means a compound having both a hydrophilic group and a hydrophobic group in one molecule, and a surfactant may be appropriately added as necessary to an emulsion such as O/W emulsion and W/O emulsion.

In one embodiment of the present invention, because the complex of the present invention has an emulsifying ability, preferably, emulsions such as O/W emulsion and W/O emulsion are substantially free of surfactant. This makes it possible to provide an emulsifier and an emulsion having less stickiness derived from emulsifier, and furthermore, less irritation.

Here, "substantially free of" means that the surfactant is not contained in an amount sufficient for the emulsification of an emulsion such as O/W emulsion and W/O emulsion. In addition, in the present invention, "substantially free of surfactant" means that it comprises no surfactant at all or comprises a surfactant in an amount that does not emulsify. The amount that does not emulsify can be appropriately determined by a person skilled in the art according to the compositional ratio, for example, in one embodiment it is less than 2.0 mass %, in another embodiment it is less than 0.2 mass %, or less than 0.02 mass %.

In a particular embodiment of the invention, the conditioning composition is an emulsion composition such as O/W emulsion composition and W/O emulsion composition substantially free of surfactant such as cationic surfactant.

<Other Components>

The emulsion of the present invention may comprise any components used in external preparations such as cosmetics, etc.

Examples of these additional components include ultraviolet absorbers such as ethylhexyl methoxycinnamate, hexyl diethylaminohydroxybenzoylbenzoate; thickeners and gelling agents such as dextrin palmitate, xanthan gum; quality maintaining components such as antioxidant, preservative; skin softeners (emollients); medicinal components and active components such as whitening agent, anti-wrinkle agent, antioxidative agent; fragrances, coloring agents such as pigment and dyestuff, and the like.

The blending amount of the component (A) in the emulsion can be appropriately selected depending on the emulsification type, the kind and amount of an oil agent to be used, and the viscosity required, etc.

The blending amount of the component (A) in the O/W emulsion can be appropriately selected depending on the kind and amount of an oil agent to be used, the viscosity required, and the like, and is typically 0.1 to 10.0 mass %, preferably 0.5 to 8.0 mass %, and more preferably 1.0 to 5.0 mass %.

The blending amount of the component (A) in the W/O emulsion can be appropriately selected depending on the kind and amount of an oil agent to be used, the viscosity required, and the like, and is typically 0.1 to 15.0 mass %, preferably 0.5 to 10.0 mass %, and more preferably 1.0 to 8.0 mass %.

The blending amount of the component (B) in the emulsion can be appropriately selected depending on the emulsification type, the kind and amount of an oil agent to be used, and the viscosity required, etc.

The blending amount of the component (B) in the O/W emulsion can be appropriately selected depending on the kind and amount of an oil agent to be used, the viscosity required for the emulsion composition, and the like, and is 0.01 to 5.0 mass %, preferably 0.05 to 3.0 mass %, and more preferably 0.1 to 2.0 mass %.

The blending amount of the component (B) in the W/O emulsion can be appropriately selected depending on the kind and amount of an oil agent to be used, the viscosity required, and the like, and is typically 0.01 to 5.0 mass %, preferably 0.05 to 3.0 mass %, and more preferably 0.1 to 2.0 mass %.

By using the above-mentioned blending amounts, an emulsion composition excellent in usability and stability of emulsion such as oil-in-water type or water-in-oil type of the complex consisting of component A and component B in the present invention can be achieved.

Furthermore, it is possible to provide an emulsifying ability suitable for desired emulsification type (O/W, W/0, etc.) by selecting the ratio between component A and component B.

Here, the pH of the emulsion such as O/W emulsion and W/O emulsion of the present invention can be appropriately selected, and it is preferably about pH 5.0 to 10.0, and more preferably about pH 5.0 to 8.0. Without being bound by any theory, it is considered that, by making the pH within this range, component A and component B are appropriately hydrogen-bonded to form a complex, and the dissociation of a carboxyl group is moderate, so that excellent emulsifying ability is brought about.

The viscosity of the emulsion such as O/W emulsion and W/O emulsion of the present invention can be appropriately selected depending on the characteristics of an objective product.

In one embodiment of the present invention, from the viewpoint of obtaining a creamy emulsion, it is preferable to have a viscosity higher than 10,000 mP·s, and from the viewpoint of obtaining an emulsion in the form of milky lotion, it is preferable to have a viscosity of about 300 to 10,000 mP·s.

In one embodiment of the present invention, from the viewpoint of using an emulsion such as O/W emulsion and W/O emulsion as a cosmetic agent, the viscosity of the emulsion can be appropriately selected within the range of 300 to 1,000,000 mP·s.

The present invention provides an agent containing an amide alcohol represented by formula (I), wherein the agent is used for emulsification by forming a complex with a carboxyl group-containing polymer.

Furthermore, the present invention also provides an agent containing a carboxyl group-containing polymer, which is used for emulsification by forming a complex with an amide alcohol represented by formula (I).

Hereinafter, the present invention will be described in more detail based on examples; however, the present invention is not limited to these examples, and various modifications can be made without departing from the technical idea of the present invention. In the present specification, unless otherwise specified, % means mass %.

EXAMPLES

TABLE 1

Formulation using carboxyl group-containing polymer and amide alcohol

| Classification | Ingredient name | Basic formulation (%) |
|---|---|---|
| Base | (1) Ion exchanged water | 69.0 |
| Humectant | (2) Glycerin | 5.0 |
|  | (3) 1,3-butylene glycol | 3.0 |
| Component B | (4) Carbopol ETD2050 | 1.0 |
| Oil agent | (5) Squalane | 12.0 |
| Component A | (6) Amide alcohol* | 2.0 |
| Oil agent | (7) Hydrogenated rapeseed oil alcohol | 3.5 |
| Neutralizing agent | (8) Potassium hydroxide (10% aqueous solution) | 4.5 |
| Total |  | 100.0 |
| Emulsion particle size (μm) |  | ~5(10) |
| Viscosity (mPa · s) S64, 12 rpm |  | 942000 |
| pH |  | 6.85 |

Regarding the expression of emulsion particle size, "~5 (10)" means that it is on average 5 μm or less, but there are particles with a diameter of about 10 μm scattered in some places. Hereinafter, it is expressed in the same sense.

*As the component A, the amide alcohol of formula (I) wherein $R_1$ is unsaturated C18 alkyl (oleyl), $R_2$ is H, $R_3$ is C5, and having the following structure (I-4), was used.

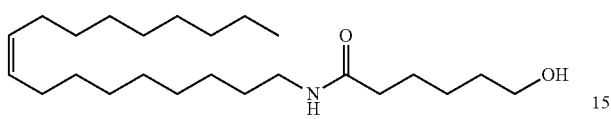

(I-4)

In the present specification, the above amide alcohol is also referred to as "amide alcohol OLH".

(Production Method)

(1) to (4) were uniformly stirred and dissolved at 80° C. to obtain an aqueous phase. Meanwhile, (5) to (7) were uniformly stirred and dissolved at 80° C. to obtain an oil phase. The obtained aqueous phase and oil phase were mixed and uniformly dissolved, and the mixture was prepared by stirring with a disperser at 80° C. While stirring the mixture, (8) was added to obtain an oil-in-water emulsion composition.

(Evaluation)

1. Measurement of Emulsion Particle Size by Microscopic Observation

Using "BX-51" manufactured by Olympus Corporation, observation was carried out at 400 times magnification, and emulsion particle sizes of the mixture before neutralization and of the emulsion after neutralization were evaluated. The results are shown in FIG. 1.

The emulsion particle size of the emulsion after neutralization is on average about 5 μm or less (there rarely are oil droplets of about 10 μm), and it can be said that a highly stable emulsion is obtained.

In addition, the emulsion was stored in a constant temperature bath at 45° C. for 1 month and visually observed 1 month later; no change was observed in the emulsified state, and the storage stability was also good.

2. Viscosity

Viscosity was measured with Brookfield viscometer: PROGRAMMABLE DV-II+VISCOMETER, using two types of SPINDLE S63 and S64 depending on the viscosity at a rotation speed of 12 rpm. The viscosity was 942,000 mPa·s. It can be said that an emulsion having a viscosity suitable for creamy cosmetic compositions and the like can be provided.

3. pH

The pH was measured with a pH meter: LAQUAact pH/ORP METER D-72 manufactured by Horiba, Ltd., pH of the emulsion was 6.85. It can be said that a stable emulsion can be provided at a pH suitable for cosmetic compositions.

For easy observation of emulsions of basic formulation, simple formulations described in Table 2 below were prepared.

TABLE 2

Simple formulation

| Classification | Ingredient name | Simple formulation (non-neutralized) | Simple formulation (neutralized) |
|---|---|---|---|
| Base | Ion exchanged water | 50.0 | 50.0 |
| Thickener | Carbopol ETD2050 | 1.0 | 1.0 |
| Oil agent | Squalane | 12.0 | 12.0 |
| Component A | Amide alcohol OLH | 2.0 | 2.0 |
| Neutralizing agent | Potassium hydroxide (10% aqueous solution) | — | 4.5 |
| | Total | 65.0 | 69.5 |
| | Emulsion particle size (μm) | — | ~5(10) |
| | Viscosity (mPa · s) S64, 12 rpm | — | 942000 |
| | pH | 3.07 | 6.85 |

Figure 2:
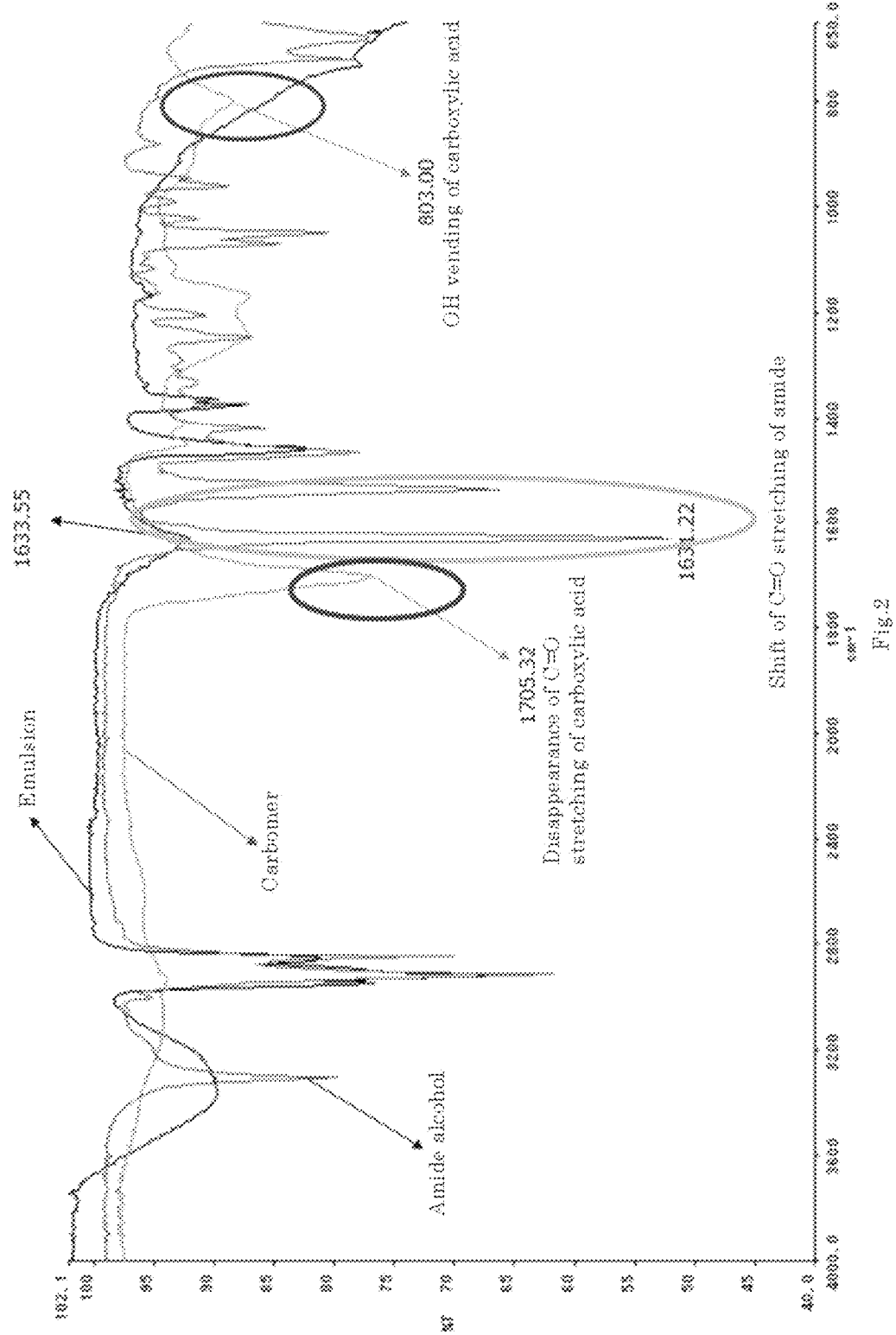
FIG. 2 is a graph showing FT-IR measurement results of amide alcohol, carbomer, and blended preparation (non-neutralized).

Preparations in which each of the two compositions: non-neutralized and neutralized compositions was naturally dried at 25° C. for 2 weeks, as well as amide alcohol and carbomer were subjected to the measurement of Fourier Transform Infrared Spectroscopy (hereinafter referred to as FT-IR) using an infrared spectrometer (Spectrum One from PerkinElmer Japan, Co., Ltd.). Measurement results of amide alcohol, carbomer and non-neutralized preparation are shown in FIG. 2, and measurement results of amide alcohol, carbomer and neutralized preparation are shown in FIG. 3.

Since O—H stretching (3300 to 2500 $cm^{-1}$) and O—H vending (1000 to 850 $cm^{-1}$) by a water molecule mask the absorption of complex formation, natural drying of the emulsion was performed to eliminate the absorption by water molecules as much as possible.

From these results, it can be understood that the absorption spectrum of the complex is different from superimposed absorption spectra of the amide alcohol alone and the carbomer alone.

In the preparation system, absorption of O—H vending of the carbomer at 803 $cm^{-1}$ disappeared, and new stretching vibration of the carboxylate ion ($COO^-$) appeared at 1400 $cm^{-1}$, and furthermore, C=O stretching of the amide bond of the amide alcohol at 1631 $cm^{-1}$ shifted to 1632 $cm^{-1}$. This indicates the following: COOH that is a part of the carboxyl groups of the carbomer is bonded to the carbonyl group C=O of the amide bond of the amide alcohol by a hydrogen bond, and carboxyl groups that are not hydrogen bonded become carboxylate ions.

Without being bound by any theory, it can be considered as follows: in the non-neutralized state of carbomer, a carboxyl group is —COOH, forming a hydrogen bond with a carbonyl group of the amide bond of the amide alcohol, and the complex is hydrophobic; as the complex is gradually neutralized, a part of the carbomer side chains dissociated into $COO^-$ to regain hydrophilicity, so the complex becomes to have both a hydrophobic part and a hydrophilic part, exhibiting higher emulsifying ability.

Without being bound by any theory, it is considered that N in the amide bond portion of the amide alcohol and the carboxyl group of the carbomer form a hydrogen bond in both non-neutralized and neutralized states. However, in a high-alkali region wherein pH is 12.0 or higher, dissociation of carboxylate ions proceeds excessively, and the hydrogen bond becomes a hydrogen bond of only the carbonyl group of the amide alcohol and the carbonyl group of the carboxyl group ion, and the complex forming force tends to be weakened; and therefore, it is considered that the viscosity of the whole preparation reduces and the emulsification performance of the whole preparation deteriorates.

Emulsions of different formulations described in each table were prepared.

TABLE 3

Formulation without blending carboxyl group-containing polymer

| Ingredient name | Comparative formulation 1 without carbomer, without higher alcohols | Comparative formulation 2 without carbomer, higher alcohols blended |
|---|---|---|
| Olive squalane | 12.0 | 12.0 |
| Amide alcohol OLH | 2.0 | 2.0 |
| Hydrogenated rapeseed oil alcohol | — | 3.5 |
| Potassium hydroxide (10% aqueous solution) | 1.5 | 1.5 |
| Ion exchanged water | 84.5 | 81.0 |
| Total | 100.0 | 100.0 |
| Emulsion particle size (μm) | Emulsifying ability | No emulsifying ability |
| Viscosity (mPa · s) | Unmeasurable due to separation | 2300 |

(Production Method)

Olive squalane, amide alcohol and hydrogenated rapeseed oil alcohol are uniformly dissolved at 80° C. to make an oil phase. Ion exchanged water heated to 80° C. was added thereto, and said oil phase pre-heated to 80° C. was heated with a disperser for preliminary emulsification, then it was neutralized by adding potassium hydroxide to prepare emulsified particles, and the composition of comparative formulation 1 was obtained.

Composition of comparative formulation 2 was obtained in the same manner as above, except that hydrogenated rapeseed oil alcohol was not used.

(Evaluation)

Figure 4:
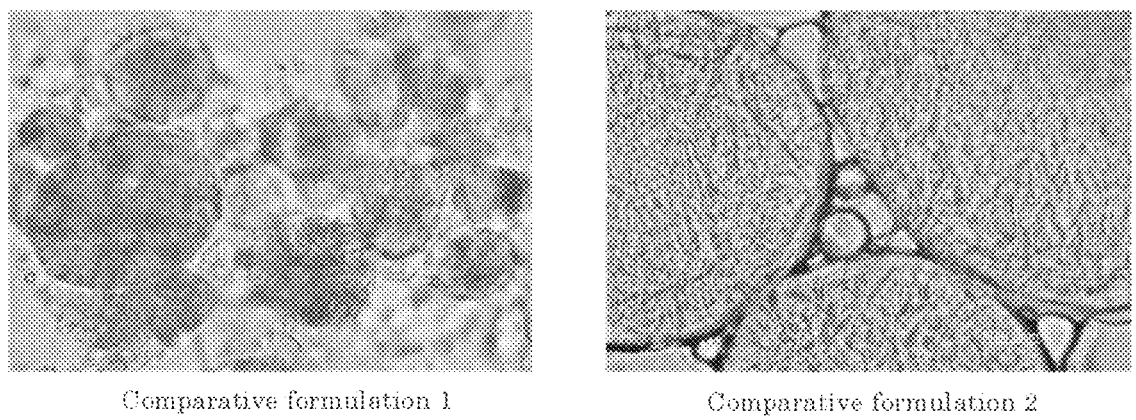
FIG. 4 is a diagram showing an emulsified state of comparative formulation 1 and comparative formulation 2.

The emulsion particle size, viscosity and pH were measured in the same manner as in Example 1. The emulsified states are shown in FIG. 4.

Comparative formulations 1 and 2 lacking carbomer did not exhibit emulsifying ability, regardless of the presence or absence of hydrogenated rapeseed oil.

TABLE 4

Presence or absence of amide alcohol

| Ingredient name | Basic formulation | Comparative formulation 3 No amide alcohol blended |
|---|---|---|
| Ion exchanged water | 72.7 | 74.7 |
| Glycerin | 5.0 | 5.0 |
| 1,3-butylene glycol | 3.0 | 3.0 |
| Carbopol ETD2050 | 0.3 | 0.3 |
| Squalane | 12.0 | 12.0 |
| Amide alcohol OLH | 2.0 | — |
| Hydrogenated rapeseed oil alcohol | 3.5 | 3.5 |
| Potassium hydroxide (10% aqueous solution) | 1.5 | 1.5 |
| Total | 100.0 | 100.0 |
| Emulsion particle size (μm) | ~10(20) | ~40 |
| Viscosity (mPa · s) S64, 12 rpm | 238000 | 12047 |
| pH | 6.58 | 6.83 |

(Production Method and Evaluation)

Comparative formulation 3 was prepared in the same manner as in Example 1, except that no amide alcohol was added.

Figure 5:
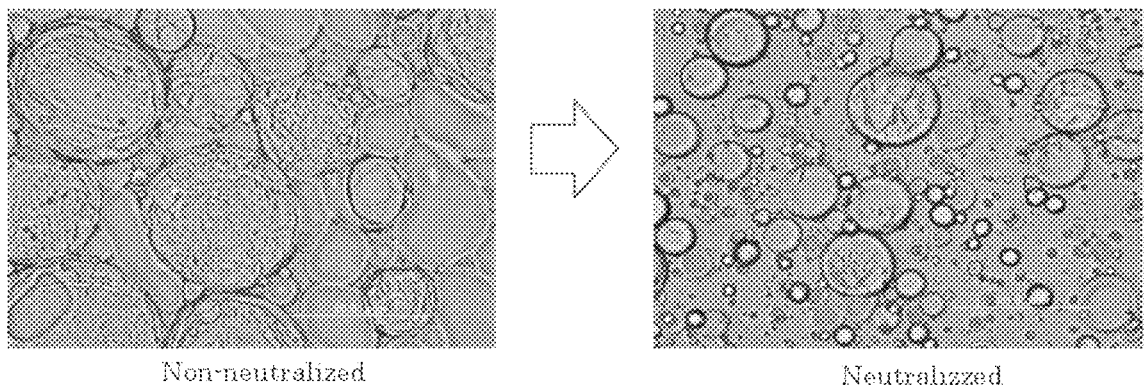
FIG. 5 is a diagram showing an emulsified state of comparative formulation 3 before neutralization and after neutralization.
Figure 6:
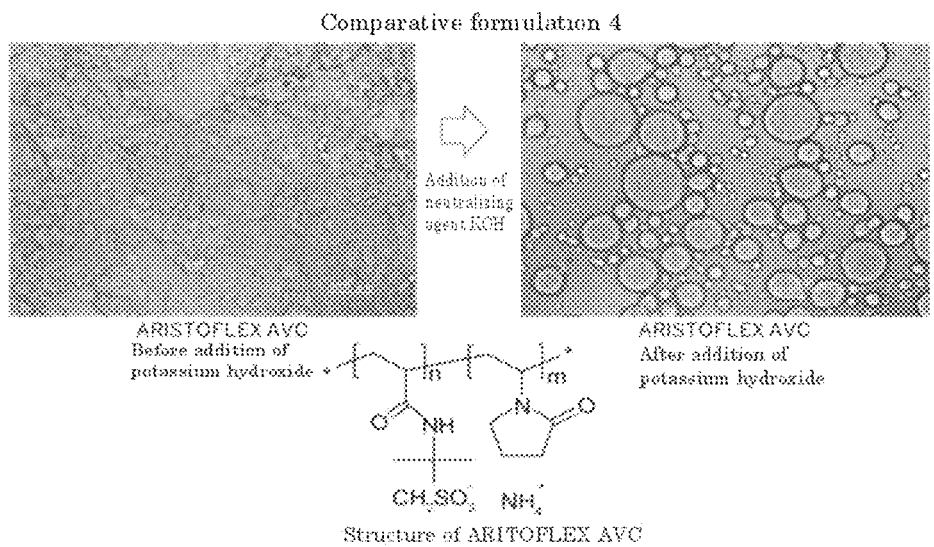

The emulsion particle size, viscosity and pH were measured in the same manner as in Example 1. The emulsified states before neutralization and after neutralization are shown in FIG. 5.

Comparative formulation 3 lacking amide alcohol has emulsifying properties, but it has a large emulsion particle size and lacks stability as an emulsion. On the other hand, a stable emulsion was obtained in the basic formulation 1 comprising amide alcohol.

TABLE 5

Examination of different thickeners

| Ingredient name | Basic formulation | Comparative formulation 4 |
|---|---|---|
| Ion exchanged water | 72.7 | 73.2 |
| Glycerin | 5.0 | 5.,0 |
| 1,3-butylene glycol | 3.0 | 3.0 |
| ARISTOFLEX AVC | — | 0.3 |
| Carbopol ETD2050 | 0.3 | — |
| Squalane | 12.0 | 12.0 |
| Amide alcohol OLH | 2.0 | 2.0 |
| Alcohol No. 20-B | 3.5 | 3.5 |
| Sodium hydroxide (10% aqueous solution) | 1.5 | 1.00 |
| Total | 100.0 | 100.0 |
| Emulsion particle size (μm) | ~10(20) | ~80 |
| Viscosity (mPa · s) | 238000 | 9900 ⇒2050 after addition of sodium hydroxide |
| pH | 6.58 | 7.91 ⇒10.89 |

(Production Method and Evaluation)

Comparative formulation 4 was prepared in the same manner as in Example 1, except that ARISTOFLEX AVC which is a polymeric thickener containing a sulfone group was used instead of carbomer.

Figure 6:
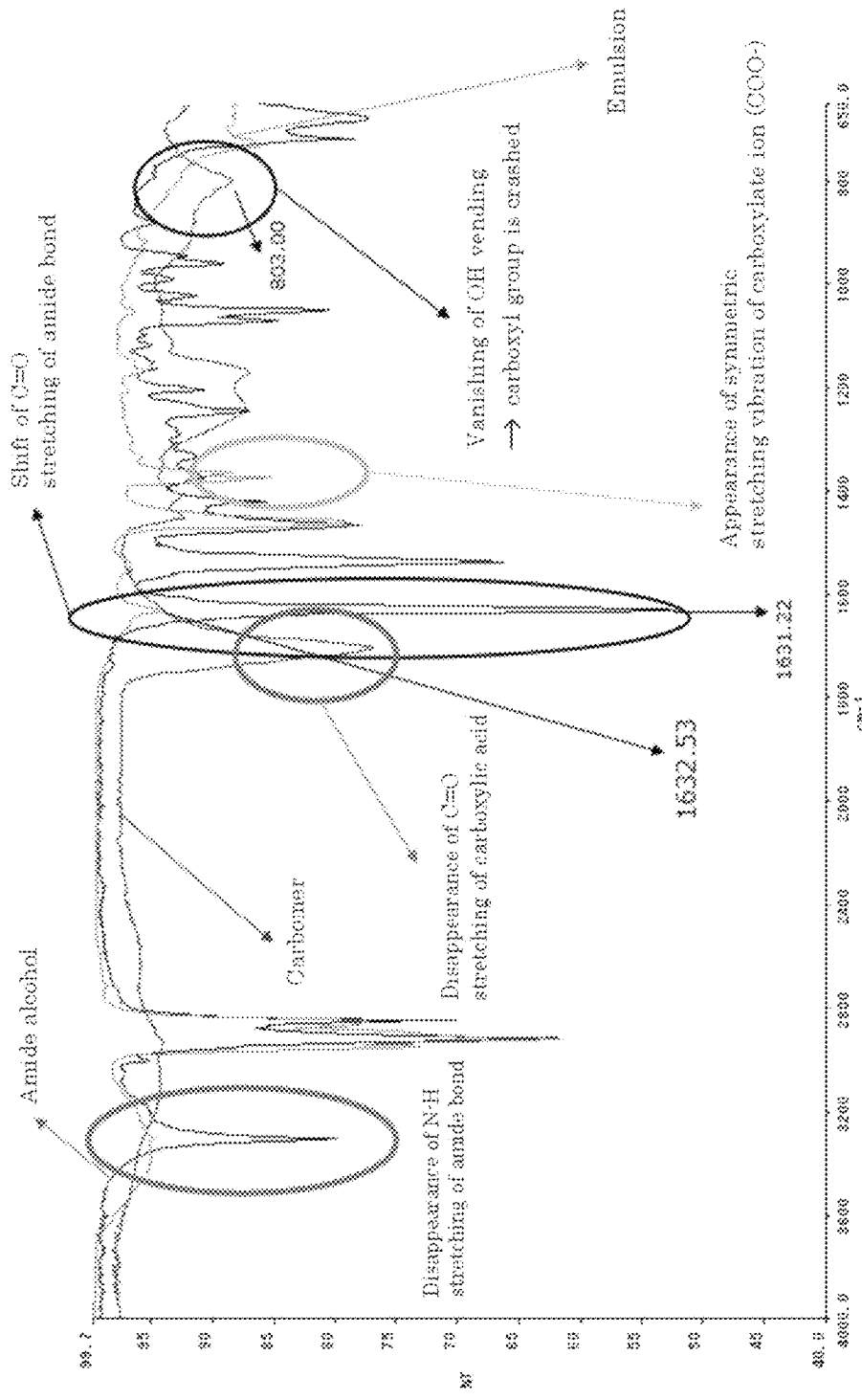
FIG. 6 is a diagram showing an emulsified state of comparative formulation 4 before neutralization and after neutralization, and the structure of the thickener used.

The emulsion particle size, viscosity and pH were measured in the same manner as in Example 1. The emulsified states before neutralization and after neutralization are shown in FIG. 6.

The synergistic effect between the sulfone group-containing polymer thickener and the amide alcohol was weak, and a stable emulsion could not be obtained.

TABLE 6

Examination of different thickeners

| Classification | Ingredient name | Basic formulation | Comparative formulation 6 | Comparative formulation 7 |
|---|---|---|---|---|
| Base | Ion exchanged water | 72.7 | 74.2 | 76.2 |
| Humectant | Glycerin | 5.0 | 5.0 | 5.0 |
|  | 1,3-butylene glycol | 3.0 | 3.0 | 3.0 |
| Component (B) Thickener | Carbopol ETD2050 | 0.3 | — | — |
|  | ARISTOFLEX HMB | — | 0.3 | 0.3 |
| Oil agent | Squalane | 12 | 12 | 12 |
| Component (A) | Amide alcohol OLH | 2.0 | 2.0 | — |
| Oil agent | Alcohol No | 3.5 | 3.5 | 3.5 |

TABLE 6-continued

Examination of different thickeners

| Classification | Ingredient name | Basic formulation | Comparative formulation 6 | Comparative formulation 7 |
|---|---|---|---|---|
| Neutralizing agent | 20-B Potassium hydroxide (10% aqueous solution) | 1.5 | — | — |
| | Total | 100.0 | 100.0 | 100.0 |
| | Emulsion particle size (μm) | ~10(20) | ~30(50) | ~30(50) |
| | Viscosity (mPa · s) | 238000 (S64, 12 rpm) | 1590 (S63, 12 rpm) | 7368 (S63, 12 rpm) |
| | pH | 6.58 | 7.79 | 6.76 |

(Production Method and Evaluation)

Comparative formulations 6 and 7 were prepared in the same manner as in Example 1, except that ARISTOFLEX HMB which is a polymeric thickener containing a sulfone group was used instead of carbomer and no neutralizing agent was added.

The emulsion particle size, viscosity and pH were measured in the same manner as in Example 1. The emulsified states are shown in FIG. 7 and FIG. 8.

Comparative formulations 6 and 7 in which component B was replaced with another water-soluble thickener showed emulsifying properties; however, the emulsion particle size was large and a stable emulsion could not be obtained.

TABLE 7

Examination of different neutralizing agents

| Classification | Ingredient name | Basic formulation | Basic formulation 2 |
|---|---|---|---|
| Base | Ion exchanged water | 72.7 | 74.05 |
| Humectant | Glycerin | 5.0 | 5.0 |
| | 1,3-butylene glycol | 3.0 | 3.0 |
| Component (B) | Carbopol ETD2050 | 0.3 | 0.3 |
| Oil agent | Squalane | 12.0 | 12.0 |
| Component (A) | Amide alcohol OLH | 2.0 | 2.0 |
| Oil agent | Alcohol No. 20-B | 3.5 | 3.5 |
| Neutralizing agent | Potassium hydroxide (10% aqueous solution) | 1.5 | — |
| | Triethanolamine | — | 0.15 |
| | Total | 100.0 | 100.00 |
| | Emulsion particle size (μm) | ~10(20) | ~10(20) |
| | Viscosity (mPa · s) S64, 12 rpm | 238000 | 7148 |
| | pH | 6.58 | 6.07 |

(Production Method and Evaluation)

Basic formulation 2 was prepared in the same manner as in Example 1, except that triethanolamine was used as a neutralizing agent instead of potassium hydroxide. Basic formulation 2 showed similar emulsifying properties, although its viscosity was largely different from that of the basic formulation 1.

The emulsion particle size, viscosity and pH were measured in the same manner as in Example 1. The emulsified states before neutralization and after neutralization are shown in FIG. 9.

In addition, the emulsions were stored for 1 month in a constant temperature bath at 45° C. and visually observed 1 month later; no change was observed in the emulsified state, and storage stability was also good.

TABLE 8

Examination of different polymers

| Ingredient name | Example 3 | Comparative example 8 No amide alcohol blended |
|---|---|---|
| Ion exchanged water | 72.7 | 74.7 |
| Glycerin | 5.0 | 5.0 |
| 1,3-butylene glycol | 3.0 | 3.0 |
| Pemulen TR-2 (iwase cosfa) | 0.3 | 0.3 |
| Isodecyl pivalate *1) | 12.0 | 12.0 |
| Amide alcohol OLH | 2.0 | — |
| Alcohol No. 20-B | 3.5 | 3.5 |
| Sodium hydroxide (10%) | 1.5 | 1.5 |
| Total | 100.0 | 100.0 |
| Emulsion particle size (μm) | ~15 | ~30 |
| Viscosity (mPa · s) S64, 12 rpm | 9598 | 9848 |
| pH | 7.61 | 6.75 |

*1) Trade name: Neolight 100P (Kokyu Alcohol Kogyo Co., Ltd.) (Production method)

An emulsion of Example 3 was prepared in the same manner as in Example 1, except that Pemulen TR-2 was used as the component B instead of carbomer.

In addition, an emulsion of Comparative example 8 was prepared in the same manner as in Example 3, except that no amide alcohol was added.

(Evaluation)

The emulsion particle size, viscosity and pH were measured in the same manner as in Example 1. The emulsified states before neutralization and after neutralization are shown in FIG. 10.

Compared with Comparative example 8 in which "Acrylates/C10-30 Alkyl Acrylates Crosspolymer" that is generally used as a polymeric emulsifier is used alone, Example 3 in which an amide alcohol of the structural formula (I) is used in combination exerts a synergistic effect with "Acrylates/C10-30 Alkyl Acrylates Crosspolymer", showing that emulsifying properties are improved.

The viscosity is 9,598 mPa·s, and it can be said that it is possible to provide an emulsion having a viscosity suitable for cosmetic compositions in the form of milky lotion, etc.

In addition, the emulsion was stored for 1 month in a constant temperature bath at 45° C. and visually observed 1 month later; no change was observed in the emulsified state, and the storage stability was also good.

Examination of different amide alcohols

| Ingredient name | Basic formulation | Example A | Example B | Example C |
|---|---|---|---|---|
| Ion exchanged water | 72.7 | 72.7 | 72.7 | 72.7 |
| Glycerin | 5.0 | 5.0 | 5.0 | 5.0 |
| 1,3-butylene glycol | 3.0 | 3.0 | 3.0 | 3.0 |
| Carbopol ET02050 | 0.3 | 0.3 | 0.3 | 0.3 |
| Squalane | 12.0 | 12.0 | 12.0 | 12.0 |
| Amide alcohol OLH | 2.0 | — | — | — |
| Amide alcohol LH | — | 2.0 | — | — |
| Amide alcohol LB | — | — | 2.0 | — |
| Amide alcohol OLB | — | — | — | 2.0 |
| Alcohol No. 20-B | 3.5 | 3.5 | 3.5 | 3.5 |

-continued

| Examination of different amide alcohols | | | | |
|---|---|---|---|---|
| Ingredient name | Basic formulation | Example A | Example B | Example C |
| Potassium hydroxide (10% aqueous solution) | 1.5 | 1.5 | 1.5 | 1.5 |
| Total | 100.0 | 100.0 | 100.0 | 100.0 |
| Emulsion particle size (μm) | ~10(20) | ~5(20) | ~3(5) | ~5(10) |
| Viscosity (mPa · s) | 238000 | 48960 | 44690 | 9948 |
| pH | 6.58 | 6.77 | 6.81 | 7.32 |
| Note | Next day pH 6.44 | — | — | — |

(Production Method and Evaluation)

Emulsions of Examples A, B and C were prepared in the same manner as in Example 1, except that the following is used as the component A instead of amide alcohol OLH:

Example A: an amide alcohol of formula (I) wherein $R_1$ is C12 alkyl, $R_2$ is H, $R_3$ is C5 (formula (I-3) below, herein also referred to as "amide alcohol LH"), or Example B: an amide alcohol of formula (I) wherein $R_1$ is C12 alkyl, $R_2$ is H, $R_3$ is C3 (formula (I-2) below, herein also referred to as "amide alcohol LB"), Example C: an amide alcohol of formula (I) wherein $R_1$ is C18 alkyl (oleyl), $R_2$ is H, $R_3$ is C3 (formula (I-1) below, herein also referred to as "amide alcohol OLB"):

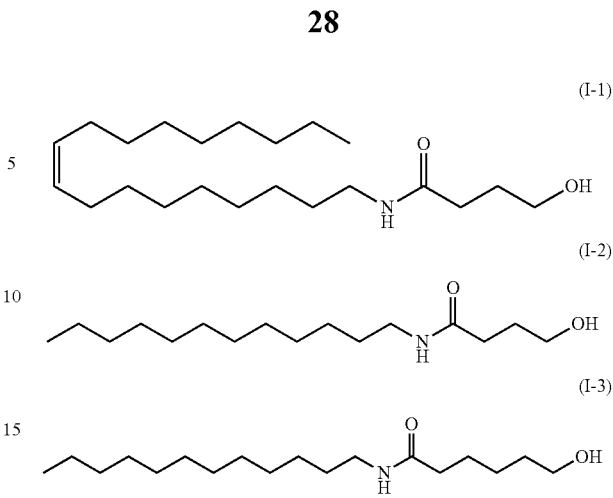

The emulsion particle size, viscosity and pH were measured in the same manner as in Example 1. The emulsified states before neutralization and after neutralization are shown in FIG. 11.

The obtained emulsions showed good emulsifying properties.

In Examples 1 to 3 and Examples A, B and C, emulsions containing hydrocarbon oil as an oil agent were prepared; stability of emulsions using other oil agents was examined.

TABLE 10

| Examination of different oil agents (ester oil) | | | | | | | | | | |
|---|---|---|---|---|---|---|---|---|---|---|
| Ingredient name | Ex. 4 | Ex. 5 | Ex. 6 | Ex. 7 | Ex. 8 | Ex. 9 | Ex. 10 | Ex. 11 | Ex. 12 | Ex. 13 |
| Ion exchanged water | 72.7 | 72.7 | 72.7 | 72.7 | 72.7 | 72.7 | 72.7 | 72.7 | 72.7 | 72.7 |
| Glycerin | 5.0 | 5.0 | 5.0 | 5.0 | 5.0 | 5.0 | 5.0 | 5.0 | 5.0 | 5.0 |
| 1,3-butylene glycol | 3.0 | 3.0 | 3.0 | 3.0 | 3.0 | 3.0 | 3.0 | 3.0 | 3.0 | 3.0 |
| Carbopol ETD2050 | 0.3 | 0.3 | 0.3 | 0.3 | 0.3 | 0.3 | 0.3 | 0.3 | 0.3 | 0.3 |
| Tricyclodecane methyl isononanoate *2) | 12.0 | — | — | — | — | — | — | — | — | — |
| Ceryl ethylhexanoate *3) | — | 12.0 | — | — | — | — | — | — | — | — |
| Diisobutyl adipate *4) | — | — | 12.0 | — | — | — | — | — | — | — |
| Hexyldecyl ethylhexanoate *5) | — | — | — | 12.0 | — | — | — | — | — | — |
| Isobutyl isostearate *6) | — | — | — | — | 12.0 | — | — | — | — | — |
| Triethylhexanoin *7) | — | — | — | — | — | 12.0 | — | — | — | — |
| Hexyldecyl isostearate *8) | — | — | — | — | — | — | 12.0 | — | — | — |
| Ethylhexyl hydroxystearate *9) | — | — | — | — | — | — | — | 12.0 | — | — |
| Pentaerythrityl tetraisostearate *10) | — | — | — | — | — | — | — | — | 12.0 | — |
| Pentaerythrityl hexaisononanoate *11) | — | — | — | — | — | — | — | — | — | 12.0 |
| Amide alcohol OLH | 2.0 | 2.0 | 2.0 | 2.0 | 2.0 | 2.0 | 2.0 | 2.0 | 2.0 | 2.0 |
| Alcohol No. 20-B | 3.5 | 3.5 | 3.5 | 3.5 | 3.5 | 3.5 | 3.5 | 3.5 | 3.5 | 3.5 |
| Sodium hydroxide (10% aqueous solution) | 1.5 | 1.5 | 1.5 | 1.5 | 1.5 | 1.5 | 1.5 | 1.5 | 1.5 | 1.5 |
| Total | 100.0 | 100.0 | 100.0 | 100.0 | 100.0 | 100.0 | 100.0 | 100.0 | 100.0 | 100.0 |
| Emulsion particle size (μm) | ~10 (15) | ~5 (10) | ~5 (20) | ~10 (20) | ~10 (15) | ~10 (20) | ~5 (10) | ~10 (20) | ~10 (20) | ~5 (10) |

TABLE 10-continued

Examination of different oil agents (ester oil)

| Ingredient name | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|
| Viscosity (mPa · s) S64, 12 rpm | 10498 | 10448 | 9898 | 17746 | 13797 | 14597 | 18446 | 15097 | 24945 | 35942 |
| pH | 7.15 | 6.56 | 6.97 | 6.76 | 7.09 | 6.93 | 6.89 | 7.14 | 6.68 | 7.33 |

*2) Trade name: KAK TCIN, Kokyu Alcohol Kogyo Co., Ltd.
*3) Trade name: CEH, Kokyu Alcohol Kogyo Co., Ltd.
*4) Trade name: KAK DIBA, Kokyu Alcohol Kogyo Co., Ltd.
*5) Trade name: ICEH, Kokyu Alcohol Kogyo Co., Ltd.
*6) Trade name: KAK IBIS, Kokyu Alcohol Kogyo Co., Ltd.
*7) Trade name: TOG, Kokyu Alcohol Kogyo Co., Ltd.
*8) Trade name: ICIS, Kokyu Alcohol Kogyo Co., Ltd.
*9) Trade name: Risocast IOHS, Kokyu Alcohol Kogyo Co., Ltd.
*10) Trade name: KAK PTI, Kokyu Alcohol Kogyo Co., Ltd.
*11) Trade name: Hailucent DPIN 6, Kogyu Alcohol Kogyo Co., Ltd.

TABLE 11

Examination of different oil agents (silicone oil)

| Ingredient name | Ex. 14 | Ex. 15 | Ex. 16 | Ex. 17 | Ex. 18 | Ex. 19 | Ex. 20 |
|---|---|---|---|---|---|---|---|
| Ion exchanged water | 72.7 | 72.7 | 72.7 | 72.7 | 72.7 | 72.7 | 72.7 |
| Glycerin | 5.0 | 5.0 | 5.0 | 5.0 | 5.0 | 5.0 | 5.0 |
| 1,3-butylene glycol | 3.0 | 3.0 | 3.0 | 3.0 | 3.0 | 3.0 | 3.0 |
| Carbopol ETD2050 | 0.3 | 0.3 | 0.3 | 0.3 | 0.3 | 0.3 | 0.3 |
| Dimethicone 5 mPa · s *12) | 12.0 | — | — | — | — | — | — |
| Dimethicone 10 mPa · s *13) | — | 12.0 | — | — | — | — | — |
| Dimethicone 20 mPa · s *14) | — | — | 12.0 | — | — | — | — |
| Dimethicone 50 mPa · s *15) | — | — | — | 12.0 | — | — | — |
| Dimethicone 100 mPa · s *16) | — | — | — | — | 12.0 | — | — |
| Diphenyl dimethicone *17) | — | — | — | — | — | 12.0 | — |
| Dimethicone 1000 mPa · s *18) | — | — | — | — | — | — | 12.0 |
| Amide alcohol OLH | 2.0 | 2.0 | 2.0 | 2.0 | 2.0 | 2.0 | 2.0 |
| Alcohol No. 20-B | 3.5 | 3.5 | 3.5 | 3.5 | 3.5 | 3.5 | 3.5 |
| Potassium hydroxide (10% aqueous solution) | 1.5 | 1.5 | 1.5 | 1.5 | 1.5 | 1.5 | 1.5 |
| Total | 100.0 | 100.0 | 100.0 | 100.0 | 100.0 | 100.0 | 100.0 |
| Emulsion particle size (μm) | ~5 (10) | ~5 (15) | ~5 (15) | ~10 (20) | ~10 (20) | ~10 (20) | ~20 (50) |
| Viscosity (mPa · s) S64, 12 rpm | 28644 | 162000* | 46340 | 20446 | 20596 | 25045 | 20796 |
| pH | 6.95 | 6.96 | 7.23 | 6.98 | 7.18 | 6.83 | 6.51 |

*measuring condition: S64, 3 rpm
*12) Trade name: Element 14 PDMS 5-JC, Momentive Performance Materials Japan Limited Liability Co.
*13) Trade name: Element 14 PDMS 10-JC, Momentive Performance Materials Japan Limited Liability Co.
*14) Trade name: Element 14 PDMS 20-JC, Momentive Performance Materials Japan Limited Liability Co.
*15) Trade name: Element 14 PDMS 50-JC, Momentive Performance Materials Japan Limited Liability Co.
*16) Trade name: Element 14 PDMS 100-JC, Momentive Performance Materials Japan Limited Liability Co.
*17) Trade name: TSF 437, Momentive Performance Materials Japan Limited Liability Co.
*18) Trade name Element 14 PDMS 1000-JC, Momentive Performance Materials Japan Limited Liability Co.

(Production Method and Evaluation)

Emulsions of Examples 4 to 22 were prepared in the same manner as in Example 1, except that the ester oil or silicone oil described in the table was used instead of squalane.

The emulsion particle size, viscosity and pH were measured in the same manner as in Example 1. For several formulations, the emulsified states are shown in FIG. 12 and FIG. 13.

The emulsions comprising various oil agents showed stable emulsifying properties.

The emulsions of the above Examples 4 to 13 were stored in a constant temperature bath at 45° C. for 1 month and visually observed 1 month later; no change was observed in the emulsified state, and the storage stability was also good.

From this fact, it can be understood that the complex of the present invention is suitable for preparing emulsions using any oil agent.

Incidentally, in the formulation using dimethicone 1000 cs, while the emulsified particles are larger as compared with the other Examples, emulsification is remarkably promoted as compared with the cases before neutralization. The amount of dimethicone 1000 cs used in a general emulsification formulation is less than 12%, and it can be said that practical use is possible.

TABLE 12

Comparison with nonionic surfactant

| Ingredient name | Example 1 | Comparative example 9 | Comparative example 10 |
|---|---|---|---|
| Ion exhanged water | 72.7 | 72.7 | 72.7 |
| Glycerin | 5.0 | 5.0 | 5.0 |
| 1,3-butylene glycol | 3.0 | 3.0 | 3.0 |
| Carbopol ETD2050 | 0.3 | 0.3 | 0.3 |
| Squalane | 12.0 | 12.0 | 12.0 |
| Amide alcohol OLH | 2.0 | — | — |
| Emalex 820 | — | 2.0 | — |
| Emalex 805 | — | — | 2.0 |
| Alcohol No. 20-B | 3.5 | 3.5 | 3.5 |
| Potassium hydroxide (10%) | 1.5 | 1.5 | 1.5 |
| Total | 100.0 | 100.0 | 100.0 |
| Emulsion particle size (μm) | ~20 | ~15 | ~40 |
| pH | 6.9 | 6.7 | 6.5 |
| Viscosity (mPa · s) S64, 12 rpm, 25° C. | 38000 | 32000 | 43000 |
| Note | Many polarized particles | Less polarization | Polarization is moderate, many bubbles |

(Production Method)

Emulsions of Comparative examples 9 and 10 were prepared in the same manner as in Example 1, except that a commonly used nonionic surfactant was used instead of amide alcohol.

(Evaluation)

1. Comparison of Emulsifying Properties by Microscopic Observation

Evaluation was carried out using "BX-51" (40 times magnification) manufactured by Olympus Corporation and a digital microscope "VHX-6000" (300 times magnification) manufactured by Keyence Corporation.

Figure 14:
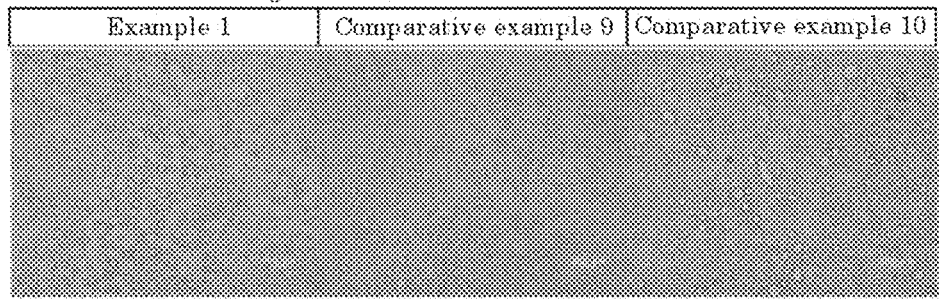
FIG. 14 is a diagram showing an emulsified state of Example 1, Comparative example 9 and Comparative example 10 observed with "BX-51" manufactured by Olympus Corporation at 40 times magnification.
Figure 15:
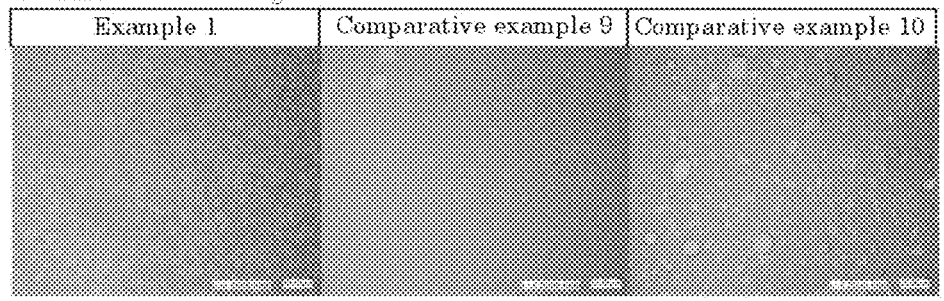
FIG. 15 is a diagram showing an emulsified state of Example 1, Comparative example 9 and Comparative example 10 observed with a digital microscope "VHX-6000" manufactured by Keyence Corporation at 300 times magnification.

Respective results are shown in FIG. 14 and FIG. 15.

It can be seen that in terms of emulsion particle size, the emulsion according to the present invention has emulsifying properties comparable to that of the emulsions using a commonly-used nonionic surfactant.

2. Evaluation of Slipperiness by Friction Tester

Measurement was carried out using Friction Tester KES-SE (Kato Tech Co., Ltd.) and the following:
sample stage temperature: 35±1° C.,
load: 25 g,
detecting part: silicone contact,
artificial leather: artificial leather Suprare (Idemitsu Techno Fine Co., Ltd.),
and with 10 times application (detection was performed only during the application in the forward direction).

Figure 16:
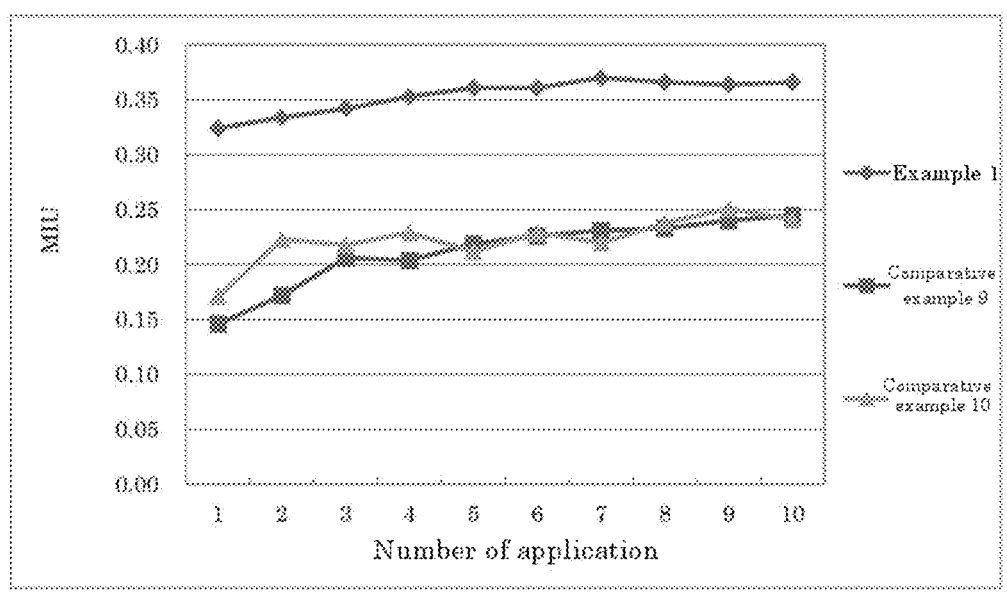
FIG. 16 is a graph showing slipperiness by a friction tester.

The results are shown in FIG. 16.

The MIU value (average friction coefficient: a higher value indicates lesser slipperiness) of the product of the present invention is higher than those of Comparative examples 9 and 10. This is because the product of the present invention does not contain a surfactant, so it does not have a slime derived from a surfactant. Consequently the MIU value becomes large, which indicates that, as the sensory evaluation, stoppage is quick and feeling of penetration is strong.

3. DSC Measurement

Figure 17:
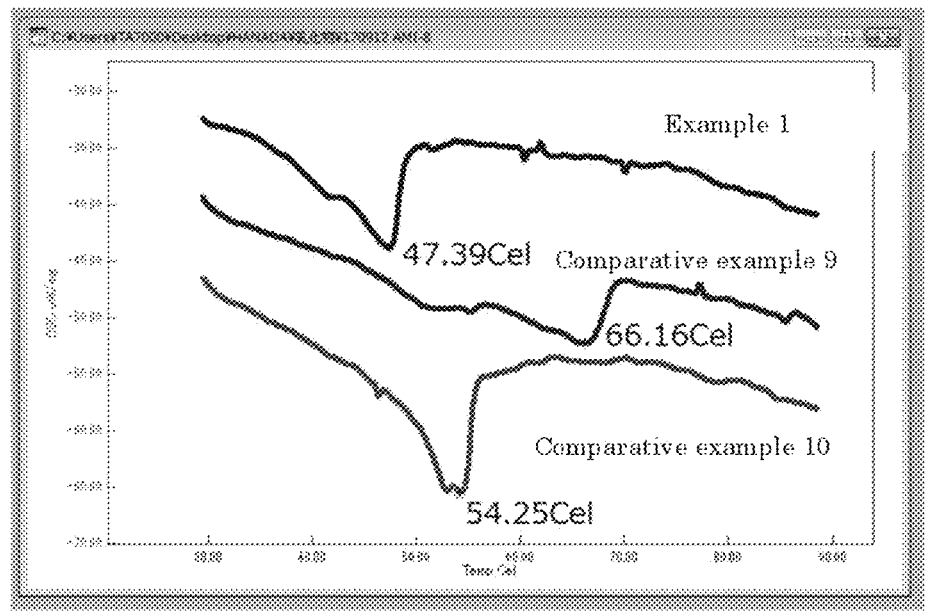
FIG. 17 is a graph showing DSC measurement results.

High sensitivity type differential scanning calorimeter DSC7000X (Hitachi High-Tech Science Corporation)
Measurement range: 30 to 90° C.
Temperature rise: 1° C./1 min The results are shown in FIG. 17.

Melting point of the emulsion of the present invention is 47.39° C., which is lower than that of Comparative examples. The product of the present invention does not contain a so-called surfactant (emulsifier). This peak is different from the absorption peak of α-gel generally formed by surfactants and higher alcohols. On the other hand, thermal absorption peaks found in Comparative examples 9 and 10 derive from general α-gels.

As described above, the oil-in-water emulsion composition obtained by utilizing the complex formed from the amide alcohol of the structural formula (I) and the polymer containing a carboxyl group in the molecule which are essential components of the present invention is completely different from conventional emulsion compositions.

4. Measurement of Viscoelasticity (Evaluation of Thixotropy by Loop Measurement)

Apparatus: Viscosity/viscoelasticity measuring apparatus HAAKE
RheoStress 6000 (Thermo Fisher Scientific Inc.)

Figure 18:
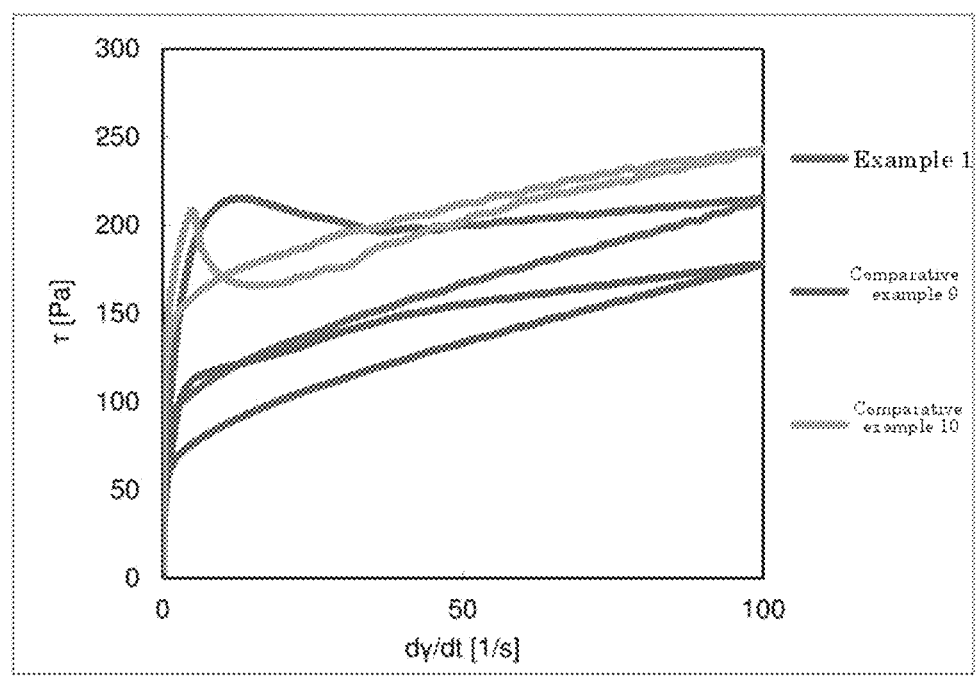
FIG. 18 is a graph showing viscoelasticity measurement results.

The results are shown in FIG. 18.

Thixotropy of the product of the present invention is shown to be larger than that of Comparative examples 9 and 10. This indicates that in the sensory evaluation, the cream exhibits a large crumbling feel at the time of application. The product of the present invention exhibits clearly different behavior from conventional products. Here, the graph line of Comparative example 10 exhibits a profile showing a yield value on the return route, and this is because the emulsion has been emulsified using a surfactant with a low HLB of 8.0, and the emulsion itself is unstable, and therefore such a profile has been shown.

In each of the above Examples, the final emulsion composition was prepared by stirring and emulsifying the aqueous phase and the oil phase, then neutralizing with the addition of a neutralizing agent, and further stirring; however, in the following Examples D to G, differences in the emulsified state were examined between a process of adding a neutralizing agent after emulsification in the same manner as above (hereinafter referred to as post-addition) and a process of neutralizing an aqueous phase containing a carboxyl-containing polymer with an alkali, adding this to an oil phase, and then stirring and emulsifying to prepare an emulsion (hereinafter referred to as pre-addition).

TABLE 13

Examination of timing of adding a neutralizing agent

| | | | Example D | Example E | Example F | Example G |
|---|---|---|---|---|---|---|
| Oil phase | 1. | Squalane | 12.0 | — | — | — |
| | | Dimethicone 5 mPa · s | — | 12.0 | — | — |
| | | Neolight 100 mPa · s | — | — | 12.0 | — |
| | | Dimethicone 10 mPa · s | — | — | — | 12.0 |
| | 2. | Alcohol No. 20-B | 3.5 | 3.5 | 3.5 | 3.5 |
| | 3. | Amide alcohol OLH | 2.0 | 2.0 | 2.0 | 2.0 |

TABLE 13-continued

Examination of timing of adding a neutralizing agent

|  |  |  | Example D | Example E | Example F | Example G |
|---|---|---|---|---|---|---|
|  | 4. | Potassium hydroxide (10%) | 1.5 | 1.5 | 1.5 | 1.5 |
| Aqueous phase | 5. | Glycerin | 5.0 | 5.0 | 5.0 | 5.0 |
|  | 6. | 1,3-butylene glycol | 3.0 | 3.0 | 3.0 | 3.0 |
|  | 7. | Carbopol ETD2050 | 0.3 | 0.3 | 0.3 | 0.3 |
|  | 8. | Ion exchanged water | 72.7 | 72.7 | 72.7 | 72.7 |
| Post-addition | | Emulsion particle size (μm) | ~10(20) | ~20(30) | ~10(20) | ~20(30) |
|  | | pH | 6.5 | 6.7 | 6.6 | 6.6 |
|  | | Viscosity (mPa · s) S64, 1.5 rpm, 25° C. | 67000 | 67000 | 54000 | 95000 |
| Pre-addition | | Emulsion particle size (μm) | ~20 | ~5(10) | ~30 | ~5(10) |
|  | | pH | 6.6 | 6.9 | 6.6 | 6.6 |
|  | | Viscosity (mPa · s) S64, 1.5 rpm, 25° C. | 160000 | 61000 | 93000 | 93000 |

The emulsion particle size, viscosity and pH were measured in the same manner as in Example 1. The emulsified states of pre-addition and post-addition are shown in FIG. 19.

It is understood that an emulsion can be prepared by any of the method of pre-addition and post-addition, although the emulsified states are different from each other due to difference in the timing of the addition of a neutralizing agent.

In each of the above Examples, an O/W emulsion was prepared; in the following Example H, a W/O emulsion was prepared.

TABLE 14

Formulation of W/O emulsion

| Classification | | Ingredient name | Example H |
|---|---|---|---|
| Aqueous phase | Base | (1) Ion exchanged water | 38.0 |
|  | Humectant | (2) Glycerin | 5.0 |
|  |  | (3) 1,3-butylene glycol | 3.0 |
|  | Component B | (4) PEMULEN TR-2 | 0.1 |
| Oil phase | Oil agent | (5) Squalane | 48.4 |
|  | Component A | (6) Amide alcohol OLH | 5.0 |
| Neutralizing agent | | (7) Potassium hydroxide (10%) | 0.5 |
| Total | | | 100.0 |
| Emulsion particle size (μm) | | | ~30(50) |
| Viscosity (mPa · s) (No. 64, 12 rpm) | | | 9700 |

(Production Method)

(1) to (4) were uniformly stirred and dissolved at 80° C. to obtain an aqueous phase. Meanwhile, (5) and (6) were uniformly stirred and dissolved at 80° C. to obtain an oil phase. The obtained aqueous phase and oil phase were mixed and uniformly dissolved, and it was stirred at 80° C. with a disperser to prepare a mixture. While stirring the mixture, (7) was added to obtain a water-in-oil emulsion composition.

Figure 20:
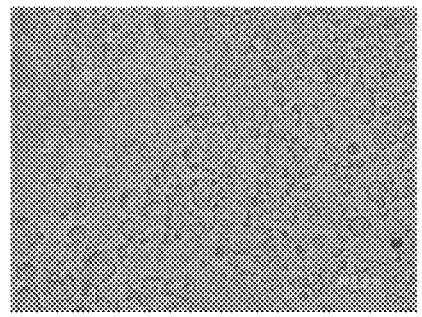
FIG. 20 is a diagram showing an emulsified state of the W/O emulsion of Example H.

The W/O emulsion was obtained from a carboxyl group-containing polymer and an amide alcohol. The emulsified state is shown in FIG. 20.

Examples of O/W emulsion cosmetic composition using the complex of the present invention are shown below.

[Example 23] Hair Treatment Lotion

TABLE 15

|  |  | Blending amount (%) |
|---|---|---|
| (1) | Propylene glycol | 2.0 |
| (2) | Glycerin | 1.0 |
| (3) | Alkyl-modified carboxyvinyl polymer (Component B) Trade name: Pemulen TR-1, Lubrizol Advanced Materials, Inc. | 0.1 |
| (4) | Amide alcohol LB (Component A) | 0.5 |
| (5) | Methylphenyl polysiloxane | 1.0 |
| (6) | Keratin hydrolyzate Trade name: Promois WK-H, Seiwa Kesei Co., Ltd. | 1.0 |
| (7) | Methylparaben | 0.1 |
| (8) | Octyl methoxycinnamate | 0.01 |
| (9) | Ethanol | 5.0 |
| (10) | Potassium hydroxide | 0.15 |
| (11) | Ion exchanged water | Balance |
| (12) | Fragrance | 0.01 |

<Production Method>

(1) to (3), (6), (7) and (11) are heated to 80° C. and uniformly dissolved (aqueous phase). Meanwhile, (4), (5) and (8) are uniformly dissolved at 80° C. to obtain an oil phase.

While adding the oil phase to the aqueous phase, it was stirred with a disperser. Then, a solution prepared with (10) and a part of (11) is added and emulsified. Upon completion of the emulsification, the mixed solution of (9) and (12) is added and cooled to normal temperature, to obtain a targeted hair treatment lotion having pH 6.2.

[Example 24] Emulsion Foundation

TABLE 16

|  |  | Blending amount (%) |
|---|---|---|
| (1) | Silicone-coated titanium oxide | 18.0 |
| (2) | Silicone-coated iron oxide (red) | 0.3 |
| (3) | Silicone-coated iron oxide (black) | 0.015 |
| (4) | Silicone-coated iron oxide (yellow) | 1.2 |
| (5) | Alkyl-modified carboxyvinyl polymer (Component B) Trade name: Pemulen TR-2, Lubrizol Advanced Materials, Inc. | 3.0 |
| (6) | Decamethylcyclopentasiloxane | 35.0 |
| (7) | Trimethylsiloxysilicate/decamethylcyclopentasiloxane solution Trade name: X-21-5250, Shin-Etsu Chemical Co., Ltd. | 5.0 |
| (8) | Amide alcohol of structural formula (I) (Component A) ($R_1$ is 2-ethylhexyl, $R_2$ is H, $R_3$ is C4) | 3.0 |
| (9) | Sodium hydroxide | 0.1 |
| (10) | ion exchanged water | Balance |

<Production Method>

(1) to (4), (6), (7) and (8) are uniformly dispersed at 80° C. (oil phase). In addition, the solution prepared with (5), (9), (10) is added and emulsified. Upon completion of the emulsification, the emulsion was cooled to normal temperature to obtain a targeted emulsion foundation having pH 6.6.

[Example 25] Milky Lotion

TABLE 17

| | | Blending amount (%) |
|---|---|---|
| (1) | Dimethicone 5cs | 10.0 |
| (2) | Squalane | 10.0 |
| (3) | Olefin oligomer | 6.0 |
| (4) | Tridecyl isononanoate<br>Trade name: KAK 139, Kokyu Alcohol Kogyo Co., Ltd. | 5.0 |
| (5) | Amide alcohol of structural formula (I) (Component A)<br>($R_1$ is octyl, $R_2$ is H, $R_3$ is C4) | 1.5 |
| (6) | Fragrance | Suitable amount |
| (7) | Dipropylene glycol | 1.0 |
| (8) | 1,3-butylene glycol | 4.0 |
| (9) | Glycerin | 6.0 |
| (10) | Carboxyvinyl polymer (Component B)<br>Trade name: Carbopol 981 Polymer, Lubrizol Advanced Materials, Inc. | 0.1 |
| (11) | Alkyl-modified carboxyvinyl polymer (Component B)<br>Trade name: Pemulen TR-2, Lubrizol Advanced Materials, Inc. | 0.1 |
| (12) | Sodium hydroxide | Suitable amount |
| (13) | Acetylated hyaluronic acid | 0.01 |
| (14) | Polymethacryloyl ethyl phosphorylcholine derivative<br>Trade name: LIPIDURE-PMB(Ph10), NOF Corporation | 0.1 |
| (15) | Equisetum arvense extract | 0.1 |
| (16) | Hamamelis virginiana (witch hazel) leaf extract | 0.1 |
| (17) | Ethanol | 5.0 |
| (18) | Phenoxyethanol | 0.3 |
| (19) | Ion exchanged water | Balance |
| (20) | Polyvinyl alcohol | 0.3 |

<Production Method>

(7) to (11) and (13) to (16) are uniformly dissolved at 80° C. (aqueous phase). Meanwhile, (1) to (5) are uniformly dissolved at 80° C., added to said aqueous phase, and stirred with a homomixer at 80° C. Next, an aqueous solution of (12) dissolved in a part of (19) is added and emulsified again with a homomixer. After completion of the emulsification, the mixed solution of (6) and (7) is added and cooled to normal temperature to obtain a targeted milky lotion having pH 6.8.

[Example 26] Emollient Cream

TABLE 18

| | | Blending amount (%) |
|---|---|---|
| (1) | Behenyl alcohol | 1.0 |
| (2) | Batyl alcohol | 0.5 |
| (3) | Hydrogenated polyisobutene | 3.0 |
| (4) | Liquid paraffin | 3.0 |
| (5) | Isostearyl neopentanoate<br>Trade name: Neolight 180P, Kokyu Alcoho Kogyo Co., Ltd. | 6.0 |
| (6) | Decamethylcyclopentasiloxane | 5.0 |
| (7) | (Dimethicone/phenylvinyl dimethicone) crosspolymer/diphenylsiloxy phenyl trimethicone mixture<br>Trade name: KSG-18A, Shin-Etsu Chemical Co., Ltd. | 0.5 |
| (8) | Fragrance | Suitable amount |
| (9) | Amide alcohol of structural formula (I) (Component A)<br>($R_1$ is C12 alkyl, $R_2$ is H, $R_3$ is C4) | 2.0 |
| (10) | Ethylparaben | 0.1 |
| (11) | Butylparaben | 0.1 |
| (12) | Tocopherol | 0.5 |
| (13) | Carboxyvinyl polymer (Component B)<br>Trade name: QUPEC 501, Sumitomo Seika Chemicals Co., Ltd. | 0.15 |
| (14) | Carboxyvinyl polymer (Component B)<br>Trade name: Synthalen L, 3V Sigma USA inc. | 0.15 |
| (15) | Polyethylene glycol 20000 | 1.0 |
| (16) | Crataegus cuneata fruit extract | 0.1 |
| (17) | Syzygium jambos leaf extract | 0.1 |
| (18) | Aloe extract | 0.1 |
| (19) | Sanguisorba officinalis root extract | 0.1 |
| (20) | Eugenia Caryophyllus (clove) flower extract | 0.1 |
| (21) | Houttuynia cordata extract | 0.1 |
| (22) | Althaea officinalis root extract | 0.1 |
| (23) | Lithospermum officinale root extract | 0.1 |
| (24) | 1,3-butylene glycol | 3.0 |
| (25) | Glycerin | 5.0 |
| (26) | Ion exchanged water | Balance |
| (27) | Potassium hydroxide | Suitable amount |

<Production Method>

(13) to (26) are uniformly dissolved at 80° C. (aqueous phase). Meanwhile, (1) to (12) are uniformly dissolved at 80° C., added to said aqueous phase, and stirred with a disperser at 80° C. Next, an aqueous solution of (27) dissolved in a part of (26) is added and emulsified again with a disperser. After completion of the emulsification, the emulsion was cooled to normal temperature to obtain a targeted emollient cream having pH 7.1.

[Example 27] Whitening Cream

TABLE 19

| | | Blending amount (%) |
|---|---|---|
| (1) | Palmitic acid | 2.0 |
| (2) | Cetyl alcohol | 1.5 |
| (3) | Vaseline | 0.5 |
| (4) | Squalane<br>Trade name: Olive squalane, Kokyu Alcohol Kogyo Co., Ltd. | 5.0 |
| (5) | Triethylhexanoin<br>Trade name: TOG, Kokyu Alcohol Kogyo Co., Ltd. | 3.0 |
| (6) | Hexyl laurate<br>Trade name: KAK HL, Kokyu Alcohol Kogyo Co., Ltd. | 2.0 |
| (7) | Amide alcohol of structural formula (I) (Component A)<br>($R_1$ is myristyl, $R_2$ is H, $R_3$ is C4 alkyl) | 2.5 |
| (8) | Fragrance | 0.1 |
| (9) | (Vinyl dimethicone/lauryl dimethicone) crosspolymer/isododecane mixture<br>Trade name: KSG-42, Shin-Etsu Chemical Co., Ltd. | 0.5 |
| (10) | Tranexamic acid | 2.0 |
| (11) | Carboxyvinyl polymer (Component B)<br>Trade name: Carbopol 980, Lubrizol Advanced Materials, Inc. | 0.5 |
| (12) | Methylparaben | 0.1 |
| (13) | Phenoxyethanol | 0.1 |
| (14) | Dimethicone 6cs | 5.0 |
| (15) | Glycerin | 3.0 |
| (16) | Hypericum perforatum extract | 0.1 |
| (17) | Melilot extract | 0.1 |
| (18) | Royal jelly extract | 0.1 |
| (19) | Ion exchanged water | Balance |

<Production Method>

(10) to (19) are uniformly heated at 80° C. (aqueous phase). Next, an oil phase of (1) to (9) is uniformly dissolved at 80° C. The oil phase heated to 80° C. is added to said aqueous phase heated to 80° C., and the mixture is emulsified by stirring with a homomixer. Upon completion of the emulsification, the emulsion was cooled to normal temperature to obtain a targeted whitening cream having pH 6.7.

[Example 28] Whitening Beauty Essence

TABLE 20

| | | Blending amount (%) |
|---|---|---|
| (1) | Di(phytosteryl-2-octyldodecyl) N-lauroyl-L-glutamate Trade name: Eldew PS-203, Ajinomoto Co., Inc. | 0.5 |
| (2) | Isodecyl neopentanoate (Trade name: Neolight 100P, Kokyu Alcohol Kogyo Co., Ltd.) | 3.0 |
| (3) | Dimethicone 5cs | 1.0 |
| (4) | Amide alcohol of structural formula (I) (Component A) ($R_1$ is 2-ethylhexyl, $R_2$ is H, $R_3$ is C4) | 4.0 |
| (5) | Alkyl-modified carboxyvinyl polymer (Component B) Trade name: Pemulen TR-1, Lubrizol Advanced Materials, Inc. | 0.1 |
| (6) | Carboxyvinyl polymer (Component B) Trade name: Carbopol ETD2050 Polymer, Lubrizol Advanced Materials, Inc. | 0.3 |
| (7) | Sodium hyaluronate | 0.1 |
| (8) | Glycerin | 5.0 |
| (9) | 1,3-butylene glycol | 3.0 |
| (10) | Ethanol | 3.0 |
| (11) | 4-isobutyl resorcinol | 0.25 |
| (12) | Ascorbic acid glucoside | 1.0 |
| (13) | Fragrance | Suitable amount |
| (14) | Potassium hydroxide | Suitable amount |
| (15) | Sodium pyrosulfite | Suitable amount |
| (16) | Ion exchanged water | Balance |

<Production Method>

(5) to (9), (11), (12), (15) and (16) are uniformly dissolved at 80° C. (aqueous phase). Next, an oil phase of (1) to (4) is uniformly dissolved at 80° C. The oil phase at 80° C. is added to said aqueous phase at 80° C. and stirred with a disperser. To this, an aqueous solution in which (14) is dissolved in a part of (16) is added and emulsified by stirring with a disperser. Upon completion of the emulsification, a mixed solution of (13) and (10) is added and cooled to normal temperature to obtain a targeted whitening beauty essence having pH 7.1.

[Example 29] Oil-in-Water Emulsion Sunscreen

TABLE 21

| | | Blending amount (%) |
|---|---|---|
| (1) | Octyl p-methoxycinnamate | 6.0 |
| (2) | Glyceryl octyl di-p-methoxycinnamate | 2.0 |
| (3) | 4-tert-butyl-4'-methoxydibenzoylmethane | 2.0 |
| (4) | Tetra(octanoate/p-methoxycinnamate) pentaerythritol | 3.0 |
| (5) | Ethylhexyl isononanoate Trade name: ES108109, Kokyu Alcohol Kogyo Co., Ltd. | 12.0 |
| (6) | Dimethicone 20cs | 3.0 |
| (7) | Squalane Trade name: Olive squalene, Kokyu Alcohol Kogyo Co., Ltd. | 3.0 |
| (8) | Amide alcohol of structural formula (I) (Component A) ($R_1$ is butyl, $R_2$ is H, $R_3$ is C4) | 2.2 |

TABLE 21-continued

| | | Blending amount (%) |
|---|---|---|
| (9) | Microcrystalline wax | 0.1 |
| (10) | Ion exchanged water | Balance |
| (11) | Dipropylene glycol | 5.0 |
| (12) | Methylparaben | 0.2 |
| (13) | Carboxyvinyl polymer (Component B) Trade name: Carbopol 981, Lubrizol Advanced Materials, Inc. | 0.3 |
| (14) | Fragrance | 0.1 |
| (15) | Triethanolamine | Suitable amount |

<Production Method>

(10) to (13) are uniformly dissolved at 80° C. (aqueous phase). Next, an oil phase of (1) to (9) and (14) is uniformly dissolved at 80° C. The oil phase at 80° C. is added to said aqueous phase heated to 80° C. and stirred with a disperser. To this, an aqueous solution in which (15) is dissolved in a part of (10) is added and emulsified again by stirring with a disperser. Upon completion of the emulsification, the emulsion is cooled to normal temperature to obtain a targeted oil-in-water emulsion sunscreen having pH 6.5.

Examples of W/O emulsion cosmetic compositions using the complex of the present invention are shown below.

[Example 30] Hair Treatment Cream

TABLE 22

| | | Blending amount (%) |
|---|---|---|
| (1) | Propylene glycol | 2.0 |
| (2) | Glycerin | 1.0 |
| (3) | Alkyl-modified carboxyvinyl polymer (Component B) Trade name: Pemulen TR-1, Lubrizol Advanced Materials, Inc. | 0.1 |
| (4) | Amide alcohol OLH of structural formula (I-4) (Component A) (compound of structural formula (I) wherein R1 is C18, R2 is H, and R3 is C5) | 3.5 |
| (5) | Squalane (Trade name: Olive squalene, Kokyu Alcohol Kogyo Co., Ltd.) | 35.0 |
| (6) | Methylphenyl polysiloxane | 1.0 |
| (7) | Organically modified clay mineral premix (Trade name: BENTONE IHD V (isohexadecane, disteardimonium hectorite, propylene carbonate), Elementis Specialties) | 4.0 |
| (8) | Isostearic acid (Trade name: HAIMARIC MKH(R), Kokyu Alcohol Kogyo Co., Ltd.) | 3.0 |
| (9) | Dextrin palmitate (Trade name: Rheopearl KL2, Rheopearl TL2, Chiba Flour Milling Co., Ltd.) | 3.0 |
| (10) | Keratin hydrolyzate Trade name: Promois. WK-H, Selwa Kesel Co., Ltd. | 1.0 |
| (11) | Methyl paraben | 0.1 |
| (12) | Octylmethoxycinnamate | 0.01 |
| (13) | Sodium hydroxide (10% aqueous solution) | 0.1 |
| (14) | Ion exchanged water | Balance |
| (15) | Fragrance | 0.1 |

<Production Method>

(4) to (9) and (12) are uniformly mixed at 80° C. (oil phase). Meanwhile, (1) to (3), (10), (11) and (14) are uniformly mixed at 80° C. (aqueous phase).

While adding the aqueous phase to the oil phase, the mixture is stirred with a disperser.

Next, (13) is added and emulsified. Upon completion of the emulsification, (15) was added and the emulsion was cooled to normal temperature to obtain a targeted viscosity of 220,000 mPa·s.

[Example 31] W/O Emulsion Foundation

TABLE 23

| | | Blending amount (%) |
|---|---|---|
| (1) | Silicone-coated titanium oxide | 18.0 |
| (2) | Silicone-coated iron oxide (red) | 0.3 |
| (3) | Silicone-coated iron oxide (black) | 0.015 |
| (4) | Silicone-coated iron oxide (yellow) | 1.2 |
| (5) | Alkyl-modified carboxyvinyl polymer (Component B) Trade name: Pemulen TR-2, Lubrizol Advanced Materials Inc. | 0.2 |
| (6) | Decamethylcyclopentasiloxane | 35.0 |
| (7) | Trimethylsiloxysilicate/decamethylcyclopentasiloxane solution Trade name: X-21-5250, Shin-Etsu Chemical Co., Ltd. | 5.0 |
| (8) | Amide alcohol LH of structural formula (I-2) (Component A) | 3.0 |
| (9) | Sodium hydroxide | 0.1 |
| (10) | Ion exchanged water | Balance |
| (11) | Disteardimonium hectorite (Trade name: BENTON 38 V, Elementis Specialties) | 5.5 |
| (12) | Isostearic acid (Trade name: Isostearic acid EX, Kokyu Alcohol Kogyo Co., Ltd.) | 5.0 |
| (13) | Dextrin palmitateihexyldecanoate (Trade name: Rheopearl WX, Chiba Flour Milling Co., Ltd.) | 3.5 |
| (14) | Fragrance | Suitable amount |
| (15) | Pentylene glycol (Trade name: Diol PD-V, Kokyu Alcohol Kogyo Co., Ltd.) | 2.00 |

<Production Method>

(1) to (4), (6) to (8), and (11) to (14) are uniformly dispersed at 80° C. (oil phase).

Meanwhile, an aqueous phase of (5), (9) and (15) is uniformly dissolved and mixed at 80° C., and while gradually adding to the previously prepared oil phase, it is stirred with a disperser.

Furthermore, a solution prepared with (9) and a part of (10) is added and emulsified. Upon completion of the emulsification, the emulsion is cooled to normal temperature to obtain a targeted W/O emulsion foundation having a viscosity of 450,000 mPa·s.

[Example 32] Emollient Cream

TABLE 24

| | | Blending amount (%) |
|---|---|---|
| (1) | Hydrogenated polyisobutene | 3.0 |
| (2) | Liquid paraffin | 3.0 |
| (3) | Isostearyl neopentanoate Trade name: Neolight 180P, Kokyu Alcohol Kogyo Co., Ltd. | 6.0 |
| (4) | Decamethylcyclopentasiloxane | 5.0 |
| (5) | (Dimethicone/phenylvinyl dimethicone) crosspolymer/ diphenylsiloxy phenyl trimethicone mixture (Trade name: KSG-18A, Shin-Etsu Chemical Co., Ltd.) | 0.5 |

TABLE 24-continued

| | | Blending amount (%) |
|---|---|---|
| (6) | Fragrance | Suitable amount |
| (7) | Amide alcohol OLB of structural formula (I-1) (Component A) | 6.0 |
| (8) | Ethylparaben | 0.1 |
| (9) | Butylparaben | 0.1 |
| (10) | Tocopherol | 0.5 |
| (11) | Alkyl-modified carboxyvinyl polymer (Component B) (Trade name: Pemulen TR-2, Lubrizol Advanced Materials, Inc.) | 0.15 |
| (12) | Carboxyvinyl polymer, (B) component (Trade name: Synthalen L, 3 V Sigma USA Inc.) | 0.15 |
| (13) | Polyethylene glycol 20000 | 1,0 |
| (14) | Crataegus cuneata fruit extract | 0.1 |
| (15) | Syzygium jambos leaf extract | 0.1 |
| (16) | Aloe extract | 0.1 |
| (17) | Sanguisorba officinalis root extract | 0.1 |
| (18) | Eugenia Caryophyllus (clove) flower extract | 0,1 |
| (19) | Houttuynia cordata extract | 0.1 |
| (20) | Althaea officinalis root extract | 0.1 |
| (21) | Lithospermum officinale root extract | 0.1 |
| (22) | 1,3-butylene glycol | 3.0 |
| (23) | Glycerin | 5.0 |
| (24) | Pentylene glycol (Trade name: Diol PD-V, Kokyu Alcohol Kogyo Co., Ltd.) | 2.0 |
| (25) | Ionexchanged water | Balance |
| (26) | Potassium hydroxide | Suitable amount |
| (27) | Organically modified clay mineral premix (Trade name: BENTONE ISD V (isododecane, disteardimonium hectorite, propylene carbonate), Elementis Specialties) | 4.0 |
| (28) | Dextrin palmitate/ethylhexanoate (Trade name: Rheopearl TT2, Chiba Flour Milling Co., Ltd.) | 3.0 |

<Production Method>

(1) to (7), (27) and (28) are heated to 80° C. and uniformly mixed (oil phase).

Meanwhile, (8) to (26) are uniformly mixed at 80° C. (aqueous phase).

While gradually adding the aqueous phase to the oil phase at 80° C. previously prepared, the mixture is stirred with a disperser.

Furthermore, a solution prepared with (26) and a part of (25) is added and emulsified. Upon completion of the emulsification, the emulsion is cooled to normal temperature to obtain a targeted W/O emulsion emollient cream having a viscosity of 280,000 mPa·s.

[Example 33] Whitening Cream

TABLE 25

| | | Blending amount (%) |
|---|---|---|
| (1) | Oleic acid | 3.5 |
| (2) | Isostearic acid (Trade name: Isostearic acid EX, Kokyu Alcohol Kogyo Co., Ltd.) | 0.5 |
| (3) | Squalane (Trade name: Olive squalene, Kokyu Alcohol Kogyo Co., Ltd.) | 25.0 |
| (4) | Triethylhexanoin (Trade name: TOG, Kokyu Alcohol Kogyo Co., Ltd.) | 3.0 |
| (5) | Hexyl laurate (Trade name: KAK HL, Kokyu Alcohol Kogyo Co., Ltd.) | 2.0 |
| (6) | Amide alcohol LH of structural formula (I-3) (Component A) | 7.0 |

TABLE 25-continued

| | | Blending amount (%) |
|---|---|---|
| (7) | Fragrance | 0.1 |
| (8) | (Vinyldimethicone/lauryldimethicone) crosspolymer/isododecane mixture (Trade name: KSG-42, Shin-Etsu Chemical Co., Ltd,) | 0.5 |
| (9) | Tranexamic acid | 2.0 |
| (10) | Alkyl-modified carboxyvinyl polymer (Component B) (Trade name: Pemulen TR-2, Lubrizol Advanced Materials, Inc.) | 0.15 |
| (11) | Methylparaben | 0.1 |
| (12) | Phenoxyethanol | 0.1 |
| (13) | Dimethicone 6cs | 5.0 |
| (14) | Glycerin (Trade name: Triol VE, Kokyu Alcohol Kogyo Co., Ltd.) | 3.0 |
| (15) | Pentylene glycol (Trade name: Diol PD-V, Kokyu Alcohol Kogyo Co., Ltd.) | 3.0 |
| (16) | Hypericum perforatum extract | 0.1 |
| (17) | Leontopodium Alpinum Extract | 0,1 |
| (18) | Royal jelly extract | 0.1 |
| (19) | Ascorbyl sodium phosphate | 0.1 |
| (20) | Ion exchanged water | Balance |
| (21) | Organically modified clay mineral premix (Trade name: BENTONE ISD V (isododecane, disteardimonium hectorite, propylene carbonate), Elementis Specialties) | 3.5 |
| (22) | Dextrin myristate (Trade name: Rheopearl MKL, Chiba Flour Milling Co , Ltd.) | 2.5 |

<Production Method>

(1) to (8), (21) and (22) are uniformly mixed at 80° C. (oil phase).

Meanwhile, (9) to (20) are heated to 80° C. and mixed uniformly (aqueous phase; since tranexamic acid has an action to increase pH, an extremely stable emulsion can be obtained without separately blending an alkali agent).

While gradually adding the aqueous phase to the oil phase at 80° C. previously prepared, the mixture is stirred with a disperser.

Upon completion of the emulsification, the emulsion is cooled to normal temperature to obtain a targeted W/O emulsion whitening cream having a viscosity of 254,000 mPa·s.

[Example 34] Whitening Beauty Essence

TABLE 26

| | | Blending amount (%) |
|---|---|---|
| (1) | Di(phytosteryl-2-octyldodecyl) N-lauroyl-L-glutamate (Trade name: Eldew PS-203, Ajinomoto Co., Inc.) | 0.5 |
| (2) | Mineral oil | 5.0 |
| (3) | Squalane (Trade name: Olive squalene, Kokyu Alcohol Kogyo Co., Ltd.) | 15.0 |
| (4) | Isododecane | 10.0 |
| (5) | Isodecyl neopentanoate (Trade name: Neolight 100P, Kokyu Alcohol Kogyo Co., Ltd.) | 3.0 |
| (6) | Dimethicone 5cs | 1.0 |
| (7) | Amide alcohol LB of structural formula (I-2) (Component A) | 5.5 |
| (8) | Alkyl-modified carboxyvinyl polymer (Component B) (Trade name: Pemulen TR-1, Lubrizol Advanced Materials, Inc.) | 0.1 |
| (9) | Carboxyvinyl polymer (Component B) (Trade name: Carbopol ETD2050 Polymer, Lubrizol Advanced Materials, Inc.) | 0.05 |
| (10) | Sodium hyaluronate | 0.1 |

TABLE 26-continued

| | | Blending amount (%) |
|---|---|---|
| (11) | Glycerin (Trade name; Triol VE, Kokyu Alcohol Kogyo Co., Ltd.) | 5.0 |
| (12) | 1,3-butylene glycol (Trade name; Haisugarcane BG, Kokyu Alcohol Kogyo Co., Ltd.) | 3.0 |
| (13) | Ethanol | 3.0 |
| (14) | 4-isobutyl resorcinol | 0.25 |
| (15) | Ascorbic acid glucoside | 1.0 |
| (16) | Fragrance | Suitable amount |
| (17) | Potassium hydroxide | Suitable amount |
| (18) | Sodium pyrosulfite | Suitable amount |
| (19) | Ion exchanged water | Balance |
| (20) | Pentylene glycol (Trade name: Diol PD-V, Kokyu Alcohol Kogyo Co., Ltd.) | 2.5 |
| (21) | Organically modified clay mineral premix (Trade name: BENTONE ISD V (isododecane, disteardimonium hectorite, propylene carbonate), Elementis Specialties) | 3.5 |
| (22) | Dextrin palmitate (Trade name: Rheopearl KL2, Chiba Hour Milling Co., Ltd.) | 2,5 |
| (23) | Isostearic acid (Trade name: lsostearic acid EX, Kokyu Alcohol Kogyo Co., Ltd.) | 4.0 |

<Production Method>

(1) to (7), (16), (21) to (23) are uniformly dissolved at 80° C. (oil phase).

Meanwhile, (8) to (21) are uniformly dissolved at 80° C. (aqueous phase). The aqueous phase at 80° C. is added to said oil phase at 80° C. and stirred with a disperser.

To this, an aqueous solution in which (17) is dissolved in apart of (19) is added and emulsified by stirring with a disperser. Upon completion of the emulsification, a mixed solution of (13) and (10) is added and cooled to normal temperature to obtain a targeted whitening beauty essence having a viscosity of 157,000 mPa·s.

[Example 35] W/O Emulsion Sunscreen

TABLE 27

| | | Blending amount (%) |
|---|---|---|
| (1) | Octyl p-methoxycinnamate | 3.0 |
| (2) | Glyceryl ethylhexanoate di-p-methoxycinnamate | 2.0 |
| (3) | 4-tert-buty1-4'-methoxydibenzoylmethane | 2.0 |
| (4) | Tetra(octanoate/p-methoxycinnamate) pentaerythritol | 3.0 |
| (5) | Ethylhexyl isononanoate (Trade name: ES108109, Kokyu Alcohol Kogyo CO., Ltd.) | 5.0 |
| (6) | Dimethicone 20cs | 3.0 |
| (7) | Squalane (Trade name: Olive squalene, Kokyu Alcohol Kogyo Co., Ltd.) | 20.0 |
| (8) | Amide alcohol OLB of structural formula (I-1) (Component A) | 2.2 |
| (9) | Glycerin (Trade name: Triol VE, Kokyu Alcohol Kogyo Co., Ltd.) | 4.0 |
| (10) | Ion exchanged water | Balance |
| (11) | Dipropylene glycol | 1.0 |
| (12) | Methylparaben | 0.2 |
| (13) | Alkyl-modified carboxyvinyl polymer (Component B) (Trade name: Pemulen TR-2, Lubrizol Advanced Materials, Inc.) | 0.1 |
| (14) | Fragrance | 0.1 |
| (15) | Triethanolamine | Suitable amount |
| (16) | Pentylene glycol (Trade name: Diol PD-V, Kokyu Alcohol Kogyo Co., Ltd.) | 2.5 |

TABLE 27-continued

| | | Blending amount (%) |
|---|---|---|
| (17) | Organically modified clay mineral premix (Trade name: BENTONE ISD V (Isododecane, disteardimonium hectorite, propylene carbonate), Elementis Specialties) | 3.5 |
| (18) | Dextrin palmitate (Trade name: Rheopearl KL2, Chiba Flour Milling Co., Ltd.) | 2.5 |
| (19) | Isostearic acid (Trade name: Isostearic acid EX, Kokyu Alcohol Kogyo Co., Ltd.) | 4.0 |

<Production Method>

(1) to (8), (14), (17) to (19) are uniformly dissolved at 80° C. (oil phase).

Meanwhile, (9) to (13) and (16) are uniformly mixed and dissolved at 80° C. (aqueous phase).

This aqueous phase is gradually added to said oil phase heated to 80° C., and stirred with a disperser.

Furthermore, (15) is added and emulsified. Upon completion of the emulsification, the emulsion is cooled to normal temperature to obtain a targeted W/O emulsion sunscreen having a viscosity of 221,000 mPa·s.

In the production methods of Examples 23, 25, 26, 28 to 32, 34 and 35, it is also possible to carry out the preparation by pre-addition of a neutralizing agent such as potassium hydroxide, triethanolamine, sodium hydroxide, etc. to the aqueous phase.

INDUSTRIAL APPLICABILITY

In the present invention, by combining an amide alcohol and a carboxyl group-containing polymer, a complex can be provided, which is capable of preparing an emulsion such as O/W emulsion and W/O emulsion using any oil agent. Furthermore, it is possible to provide a stable emulsion such as O/W emulsion and W/O emulsion.

Such emulsions can be used for applications including cosmetics.

The invention claimed is:

1. A method for producing an emulsion composition, wherein an aqueous phase containing a carboxyl group-containing polymer, and an oil phase containing an amide alcohol represented by formula (I):

$$R_1\text{-}N(R_2)\text{-}C(=O)\text{-}R_3\text{-}OH \quad (I)$$

wherein
R$_1$ is a C6-C22 hydrocarbon group,
R$_2$ is H, or a C6-C22 hydrocarbon group,
R$_3$ is a linear or branched C2-C21 hydrocarbon group,
are mixed.

2. The method according to claim 1, which comprises neutralizing by adding a neutralizing agent.

3. The method according to claim 2, wherein the aqueous phase containing the carboxyl group-containing polymer is neutralized by adding a neutralizing agent, and the aqueous phase and the oil phase are mixed.

4. The method according to claim 1, wherein the carboxyl group-containing polymer has a molecular weight of 500,000 to 3,000,000 and a carboxyl group content of 50 to 70%.

5. The method according to claim 1, wherein the carboxyl group-containing polymer is a carboxyvinyl polymer and/or an alkyl-modified carboxyvinyl polymer.

6. The method according to claim 5, wherein the carboxyl group-containing polymer is a carboxyvinyl polymer represented by formula (II):

$$-(\text{CH}(\text{COOH})-\text{CH}_2)_n- \quad (II)$$

wherein n is an integer,
and/or an alkyl-modified carboxyvinyl represented by formula (III):

$$-(\text{CH}(\text{COOH})-\text{CH}_2)_x-(\text{C}(\text{CH}_3)(\text{COOR})-\text{CH}_2)_y- \quad (III)$$

wherein x and y are each independently an integer,
R is a C10-C30 alkyl group.

7. The method according to claim 1, wherein the amide alcohol is an amide alcohol of formula (I), wherein
R$_1$ is a C10-C22 hydrocarbon group,
R$_2$ is H,
R$_3$ is a C3-C12 hydrocarbon group.

8. The method according to claim 7, wherein the amide alcohol is one or more selected from:

(I-1), (I-2), (I-3), (I-4)

9. An emulsion composition obtained by the method according to claim 1.

10. An agent containing a carboxyl group-containing polymer, wherein the agent is used for emulsification by forming a complex with an amide alcohol represented by formula (I):

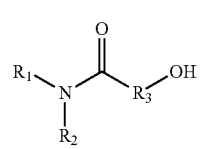
(I)
wherein
$R_1$ is a C6-C22 hydrocarbon group,
$R_2$ is H, or a C6-C22 hydrocarbon group,
$R_3$ is a linear or branched C2-C21 hydrocarbon group.
* * * * *